(12) United States Patent
Bam et al.

(10) Patent No.: US 11,504,397 B2
(45) Date of Patent: Nov. 22, 2022

(54) METHODS AND COMPOSITIONS FOR MODULATING THE WNT-SIGNALING PATHWAY AS TREATMENTS FOR INFLAMMATORY DISEASES

(71) Applicant: UNIVERSITY OF SOUTH CAROLINA, Columbia, SC (US)

(72) Inventors: Marpe Bam, Columbia, SC (US); Prakash Nagarkatti, Columbia, SC (US); Mitzi Nagarkatti, Columbia, SC (US)

(73) Assignee: University of South Carolina, Columbia, SC (US)

( * ) Notice: Subject to any disclaimer, the term of this patent is extended or adjusted under 35 U.S.C. 154(b) by 225 days.

(21) Appl. No.: 16/703,329

(22) Filed: Dec. 4, 2019

(65) Prior Publication Data
US 2020/0254020 A1 Aug. 13, 2020

Related U.S. Application Data

(60) Provisional application No. 62/802,230, filed on Feb. 7, 2019.

(51) Int. Cl.
| | | |
|---|---|---|
| *A61K 35/17* | (2015.01) | |
| *A61P 25/00* | (2006.01) | |
| *A61K 31/4709* | (2006.01) | |
| *C12N 15/113* | (2010.01) | |

(52) U.S. Cl.
CPC .......... *A61K 35/17* (2013.01); *A61K 31/4709* (2013.01); *A61P 25/00* (2018.01); *C12N 15/1138* (2013.01)

(58) Field of Classification Search
CPC ..... A61K 35/17; A61K 31/4709; A61P 25/00; C12N 15/1138
See application file for complete search history.

(56) References Cited

U.S. PATENT DOCUMENTS

| | | | | |
|---|---|---|---|---|
| 2010/0169025 A1* | 7/2010 | Arthur | ............ | G16B 25/10 702/19 |
| 2014/0073524 A1* | 3/2014 | Hood | ............ | G01N 33/6896 506/9 |
| 2015/0232837 A1* | 8/2015 | Thibonnier | ............ | A61P 29/00 435/375 |
| 2017/0009295 A1* | 1/2017 | Rigoutsos | ............ | C12Q 1/6886 |

FOREIGN PATENT DOCUMENTS

WO WO-2007074346 A2 * 7/2007 ............ A61K 31/17

OTHER PUBLICATIONS

Zhang et al., "The Risks of miRNA Therapeutics: In a Drug Target Perspective", Drug Des Devel Ther. 2021; 15: 721-733 (Year: 2021).*
Wang et al. "Posttraumatic Stress Disorder: An Immunological Disorder?", Front Psychiatry. Nov. 6, 2017;8:222 (Year: 2017).*
Tran et al. "Modulating the wnt signaling pathway with small molecules", Protein Sci. Apr. 2017;26(4):650-661 (Year: 2017).*
Shemesh et al. "Symptoms of posttraumatic stress disorder in patients who have had a myocardial infarction", Psychosomatics. May-Jun. 2006;47(3):231-9 (Year: 2006).*
O'Connell et al. "microRNA regulation of inflammatory responses", Annu Rev Immunol. 2012;30:295-312 (Year: 2012).*
Liu et al. "MiR-142-3p Attenuates the Migration of CD4+ T Cells through Regulating Actin Cytoskeleton via RAC1 and ROCK2 in Arteriosclerosis Obliterans", PLoS One. Apr. 17, 2014;9(4):e95514 (Year: 2014).*
Shi et al. "Rac1-Mediated DNA Damage and Inflammation Promote Nf2 Tumorigenesis but Also Limit Cell-Cycle Progression", Dev Cell. Nov. 21, 2016;39(4):452-465 (Year: 2016).*
Hu et al. "MicroRNA-142-3p Negatively Regulates Canonical Wnt Signaling Pathway", PLoS One. Jun. 27, 2016; 11(6):e0158432 (Year: 2016).*
Leung et al. "Characterization of cytokine gene expression in CD4+ and CD8+ T cells after activation with phorbol myristate acetate and phytohaemagglutinin", Clin Exp Immunol. Oct. 1992;90(1):147-53 (Year: 1992).*
Bam et al. "Dysregulated immune system networks in war veterans with PTSD is an outcome of altered miRNA expression and DNA methylation", Sci Rep. Aug. 11, 2016;6:31209 (Supplementary Figures) (Year: 2016).*
Al-Harthi, L. "Wnt/β-catenin and its diverse physiological cell signaling pathways in neurodegenerative and neuropsychiatric disorders" *J. Neuroimmune Pharma.* 7(4) (2012) pp. 725-730.
APA. "Diagnostic and Statistical Manual of Mental Disorders" *Am. Psych. Assoc.* DSM-V™ (2013) p. 947.
Bam, et al. "Decreased AGO2 and DCR1 in PBMCs from War Veterans with PTSD leads to diminished miRNA resulting in elevated inflammation" *Trans. Psych.* 7(8):e1222 (2017) pp. 1-10.
Bam, et al. "Evidence for Epigenetic Regulation of Pro-Inflammatory Cytokines, Interleukin-12 and Interferon Gamma, in Peripheral Blood Mononuclear Cells from PTSD Patients" *J. Neuroimmune Pharma.* 11(1) (2016) pp. 168-181.
Bam, et al. "Dysregulated immune system networks in war veterans with PTSD is an outcome of altered miRNA expression and DNA methylation" *Sci. Rep.* 6:31209 (2016) pp. 1-13.
Bauer, et al. "Inflammation in psychiatric disorders: what comes first?" *Ann. NY Acad. Sci.* 1437(1) (2019) pp. 57-67.
Bersani, et al. "A population of atypical CD56⁻CD16⁺ natural killer cells is expanded in PTSD and is associated with symptom severity" *Brain Behav. Immun.* 56 (2016) pp. 264-270.

(Continued)

*Primary Examiner* — Amy E Juedes
*Assistant Examiner* — Peter Johansen
(74) *Attorney, Agent, or Firm* — Dority & Manning, P.A.

(57) ABSTRACT

The present disclosure is directed to compositions and methods to treat the inflammatory response present in certain diseases and illnesses by modifying a dysregulation of one or more genes associated with the Wnt/β-catenin signaling pathway. Embodiments of the disclosure can provide methods for treating an inflammatory response in a patient by identifying the inflammatory response and modifying the inflammatory response.

9 Claims, 13 Drawing Sheets

Specification includes a Sequence Listing.

(56) References Cited

OTHER PUBLICATIONS

Blake, et al. "The development of a Clinician-Administered PTSD Scale" *J. Trauma Stress* 8(1) (1995) pp. 75-90.
Blanchard, et al. "Psychometric properties of the PTSD Checklist (PCL)" *Behav. Res. Ther.* 34(8) (1996) pp. 669-673.
Boscarino, J.A. "Posttraumatic stress disorder and physical illness: Results from clinical and epidemiologic studies" *Ann. NY Acad. Sci.* 1032 (2004) pp. 141-153.
Brudey, et al. "Autonomic and inflammatory consequences of posttraumatic stress disorder and the link to cardiovascular disease" *Am. J. Physio. Reg. Integr. Comp. Physio.* 309(4) (2015) pp. R315-R321.
Chen, et al. "Small molecule-mediated disruption of Wnt-dependent signaling in tissue regeneration and cancer" *Nat. Chem. Bio.* 5(2) (2009) pp. 100-107.
De Ferrari, et al. "Wnt/β-catenin signaling in Alzheimer's disease" *CNS Neuro. Dis. Drug Targ.* 13(3) (2014) pp. 1-10.
Dey, et al. "The histone demethylase KDM5b/JARID1b plays a role in cell fate decisions by blocking terminal differentiation" *Mol. Cell Bio.* 28(17) (2008) pp. 5312-5327.
Eichhorn, et al. "mRNA destabilization is the dominant effect of mammalian microRNAs by the time substantial repression ensues" *Mol. Cell* 56(1) (2014) pp. 104-115.
Freese, et al. "Integrated genome browser: visual analytics platform for genomics" *Bioinformatics* 32(14) (2016) pp. 2089-2095.
Galli, et al. "FoxOs, Wnts and oxidative stress-induced bone loss: new players in the periodontitis arena?" *J. Periodon. Res.* 46(4) (2011) pp. 397-406.
Giacoppo, et al. "Aberrant expression of beta-catenin in $CD4^+$ T cells isolated from primary progressive multiple sclerosis patients" *Neurosci. Lett.* 653 (2017) pp. 159-162.
Gilbert, S.F. "Developmental biology" 9th Ed. *Sinauer Assoc.* (2010) pp. 1-712.
Gola, et al. "Posttraumatic stress disorder is associated with an enhanced spontaneous production of pro-inflammatoiy cytokines by peripheral blood mononuclear cells" *BMC Psych.* 13 (2013) pp. 1-8.
Houschyar, et al. "Role of Wnt signaling during inflammation and sepsis: A review of the literature" *Int'l J. Artif. Organs* 41(5) (2018) pp. 247-253.
Jang, et al. "WNT/β-catenin pathway modulates the TNF-α-induced inflammatory response in bronchial epithelial cells" *Biochem. Biophys. Res. Comm.* 484(2) (2017) pp. 442-449.
Jung, et al. "Wnt2 complements Wnt/β-catenin signaling in colorectal cancer" *Oncotarget* 6(35) (2015) pp. 37257-37268.
Keerthivasan, et al. "β-Catenin promotes colitis and colon cancer through imprinting of proinflammatory properties inT cells" *Sci. Trans. Med.* 6(225) (2014) pp. 1-11.
Kessler, et al. "Prevalence, severity, and comorbidity of 12-month DSM-IV disorders in the National Comorbidity Survey Replication" *Arch. Gen. Psych.* 62(6) (2005) pp. 617-627.
Kilander, et al. "Assessment of Frizzled 6 membrane mobility by FRAP supports G protein coupling and reveals WNT-Frizzled selectivity" *Cell. Sign.* 26(9) (2014) pp. 1943-1949. (Abstract only).
Kim, et al. "TopHat2: Accurate alignment of transcriptomes in the presence of insertions, deletions and gene fusions" *Genome Bio.* 14(4):R36 (2013) pp. 1-13.
Kim, et al. "Wnt5a induces endothelial inflammation via β-catenin-independent signaling" *J. Immunol.* 185(2) (2010) pp. 1274-1282.
Kling, et al. "Roles of WNT, NOTCH, and Hedgehog signaling in the differentiation and function of innate and innate-like lymphocytes" *J. Leukoc. Bio.* 101(4) (2017) pp. 827-840.
Krämer, et al. "Causal analysis approaches in Ingenuity Pathway Analysis" *Bioinformatics* 30(4) (2014) pp. 523-530.
Kulak, et al. "Disruption of Wnt/β-Catenin Signaling and Telomeric Shortening are Inextricable Consequences of Tankyrase Inhibition in Human Cells" *Mol. Cell Bio.* 35(14) (2015) pp. 2425-2435.
Le Grand, et al. "Neural stem cells in Parkinson's disease: a role for neurogenesis defects in onset and progression" *Cell Mol. Life Sci.* 72(4) (2015) pp. 773-797.

Lemieux, et al. "Symptom severity predicts degree of T cell activation in adult women following childhood maltreatment" *Brain Behav. Immun.* 22(6) (2008) pp. 994-1003.
Li, et al. "Drugs for Autoimmune Inflammatory Diseases: From Small Molecule Compounds to Anti-TNF Biologics" *Front. Pharm.* 8(460) (2017) pp. 1-12.
Li, et al. "Wnt signaling through inhibition of β-catenin degradation in an intact Axin1 complex" *Cell* 149(6) (2012) pp. 1245-1256.
Liu, et al. "RNF6 Promotes Colorectal Cancer by Activating the Wnt/β-Catenin Pathway via Ubiquitination of TLE3" *Cancer Res.* 78(8) (2018) pp. 1958-1971.
Logan, et al. "The Wnt signaling pathway in development and disease" *Ann. Rev. Cell Dev. Bio.* 20 (2004) pp. 781-810.
Miao, et al. "Wnt signaling pathway in rheumatoid arthritis, with special emphasis on the different roles in synovial inflammation and bone remodeling" *Cell. Sign.* 25(10) (2013) pp. 2069-2078. (Abstract only).
Michopoulos, et al. "Diagnostic Biomarkers for Posttraumatic Stress Disorder: Promising Horizons from Translational Neuroscience Research" *Bio. Psych.* 78(5) (2015) pp. 344-353.
Mitchell, et al. "PTSD and obesity in the Detroit neighborhood health study" *Gen. Hosp. Psych.* 35(6) (2013) pp. 671-673.
Nusse, R. "Wnt signaling in disease and in development" *Cell Res.* 15(1) (2005) pp. 28-32.
O'Donovan, et al. "Elevated risk for autoimmune disorders in Iraq and Afghanistan veterans with posttraumatic stress disorder" *Bio. Psych.* 77(4) (2015) pp. 365-374.
Ramchand, et al. "Disparate prevalence estimates of PTSD among service members who served in Iraq and Afghanistan: Possible explanations" *J. Traum. Stress* 23(1) (2010) pp. 59-68.
Rogler, G. "Chronic ulcerative colitis and colorectal cancer" *Cancer Lett.* 345(2) (2014) pp. 235-241.
Roozen, et al. "Differential requirements for Wnt and Notch signaling in hematopoietic versus thymic niches" *Ann. NY Acad. Sci.* 1266 (2012) pp. 78-93.
Skronska-Wasek, et al. "WNT receptor signalling in lung physiology and pathology" *Pharm. Ther.* 187 (2018) pp. 150-166.
Staal, et al. "Wnt Signaling as Master Regulator of T-Lymphocyte Responses: Implications for Transplant Therapy" *Transplantation* 100(12) (2016) pp. 2584-2592.
Stalker, et al. "Ch. 27: Evaluation of histone-modifying enzymes in stem cell populations" *Meth. Mol. Bio.* 809 (2012) pp. 411-426.
Thrasivoulou, et al. "Activation of intracellular calcium by multiple Wnt ligands and translocation of β-catenin into the nucleus: A convergent model of $Wnt/Ca^{2+}$ and Wnt/β-catenin pathways" *J. Bio. Chem.* 288(50) (2013) pp. 35651-35659.
Trapnell, et al. "Transcript assembly and quantification by RNA-Seq reveals unannotated transcripts and isoform switching during cell differentiation" *Nat. Biotech.* 28(5) (2010) pp. 511-515.
Uddin, et al. "Epigenetic and immune function profiles associated with posttraumatic stress disorder" *PNAS* 107(20) (2010) pp. 9470-9475.
Villanueva, et al. "TLE3 is a dual-function transcriptional coregulator of adipogenesis" *Cell Metab.* 13(4) (2011) pp. 413-427.
Wils, et al. "Epigenetic regulation of the Hedgehog and Wnt pathways in cancer" *Crit. Rev. Oncol. Hematol.* 121 (2018) pp. 23-44.
Wysocka, et al. "A PHD finger of NURF couples histone H3 lysine 4 trimethylation with chromatin remodeling" *Nature* 442(7098) (2006) pp. 86-90.
Yoshikawa, et al. "WNT10B functional dualism: β-catenin/Tcf-dependent growth promotion or independent suppression with deregulated expression in cancer" *Mol. Biol. Cell* 18(11) (2007) pp. 4292-4303.
Zhou, et al. "Dysregulation in microRNA expression is associated with alterations in immune functions in combat veterans with post-traumatic stress disorder" *PLoS One* 9(4):e94075 (2014) pp. 1-14.

\* cited by examiner

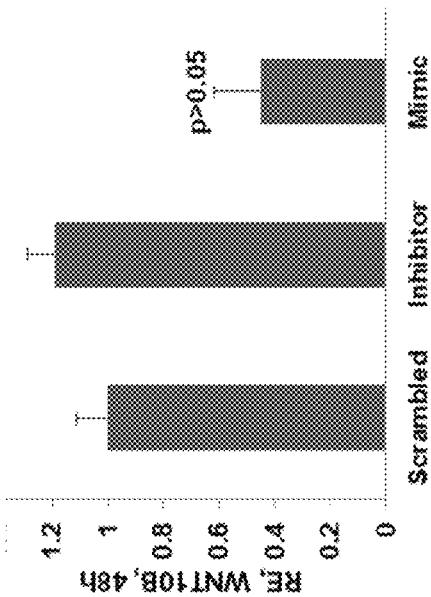
FIG. 3C
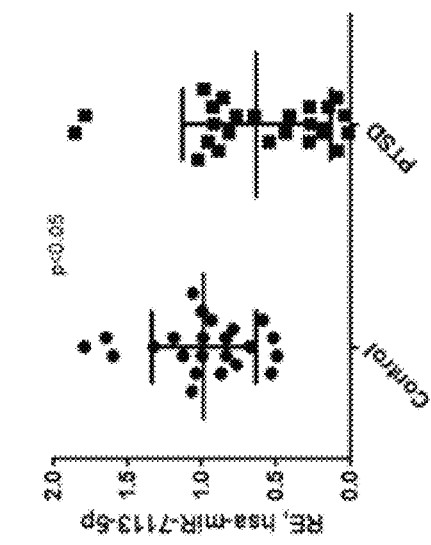
FIG. 3D
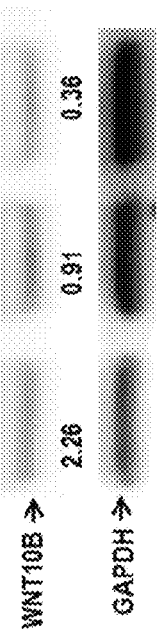
FIG. 3E
FIG. 3F

SEQUENCE LISTING

```
<160> NUMBER OF SEQ ID NOS: 2

<210> SEQ ID NO 1
<211> LENGTH: 23
<212> TYPE: RNA
<213> ORGANISM: Unknown
<220> FEATURE:
<223> OTHER INFORMATION: Description of Unknown:
      WNT10B RNA sequence

<400> SEQUENCE: 1
```

```
caaggucacu cuuggucccu gga                                          23

<210> SEQ ID NO 2
<211> LENGTH: 21
<212> TYPE: RNA
<213> ORGANISM: Homo sapiens

<400> SEQUENCE: 2
uccagggaga caguguguga g                                            21
```

METHODS AND COMPOSITIONS FOR MODULATING THE WNT-SIGNALING PATHWAY AS TREATMENTS FOR INFLAMMATORY DISEASES

CROSS REFERENCE TO RELATED APPLICATION

This application claims filing benefit of U.S. Provisional Patent Application Ser. No. 62/802,230, having a filing date of Feb. 7, 2019, which is incorporated herein by reference for all purposes.

STATEMENT AS TO RIGHTS TO INVENTIONS MADE UNDER FEDERALLY SPONSORED RESEARCH

This invention was made with Government support under Contract No. R01 AI129788, awarded by the National Institutes of Health (NIH). The Government has certain rights in the invention.

SEQUENCE LISTING

A Sequence Listing has been filed electronically in ASCII format and is hereby incorporated by reference in its entirety. Said ASCII copy, created on Jan. 27, 2020, is named USC-636_Sequence_Listing.txt and is 703 bytes in size.

BACKGROUND

The Wnt/β-catenin signaling pathway helps regulate cellular proliferation, differentiation, polarization and cell fate. While the Wnt-signaling pathway has been implicated in certain inflammatory diseases such as rheumatoid arthritis, chronic ulcerative colitis, periodontitis, lung diseases including asthma and chronic obstructive pulmonary disease, the mechanism of action remains to be characterized.

Other conditions associated with an increased inflammatory response, such as post-traumatic stress disorder (PTSD), have not been linked to alterations in the Wnt-signaling pathway. PTSD has a high prevalence among victims of traumatic events such as assault, battery, domestic abuse, and war. Approximately 3.6% of American adults between 18 to 54 years, and about 30% of Vietnam War Veterans are affected by PTSD. Also, as many as 8% of Gulf War Veterans have been diagnosed with PTSD. Prevalence of PTSD has been reported to be 14.4% in the Detroit Neighborhood Health Study (DNHS). PTSD affects social and professional functioning, emotional, along with physical health and health-related quality of life. Patients with PTSD may display not only interpersonal withdrawal but also experience increased risk of cardiovascular disease, progressive decrease in muscle bulk, osteoporosis and fractures, cancer, arthritis, and digestive disorders, the precise mechanisms of which are unclear.

There have been some reports of immune dysfunction in PTSD. Increased numbers of inflammatory immune cells have been reported in abused women with PTSD symptoms, as well as in male veterans with PTSD. In PTSD patients, there is significant increase in peripheral blood mononuclear cells (PBMCs), the number of CD4+, CD8+, NK and B cells in PBMC, and in the production of pro-inflammatory cytokines such as IFNγ, IL-17, RANTES and IL-12. Understanding the origin of chronic inflammation may help address the comorbidity associated with PTSD. Despite the observation of chronic inflammation in patients having PTSD and other diseases, the mechanisms underlying dysregulation of the immune system are not clear and treating these patients without suppressing the immune system as a whole remains a challenge.

SUMMARY OF THE INVENTION

The present disclosure is directed to compositions and methods to treat an inflammatory response that can present in certain diseases and illnesses such as PTSD, rheumatoid arthritis, chronic ulcerative colitis, periodontitis, lung diseases including asthma and chronic obstructive pulmonary disease. Embodiments of the disclosure provide methods to identify and modify a dysregulation of one or more genes associated with the Wnt/β-catenin signaling pathway (hereafter referred to as "the wnt-signaling pathway"). Some of the genes and micro-RNA involved in regulating the wnt-signaling pathway are illustrated in FIG. 3B. Thus, certain embodiments of the disclosure can provide methods for treating an inflammatory response in a patient by identifying a dysregulation in a gene or protein associated with the inflammatory response and adjusting the gene or protein expression to thereby modify the inflammatory response.

Additional embodiments can include methods for adjusting the expression or the activities of proteins involved in the wnt-signaling pathway by delivering a compound to an immune cell such as a peripheral mononuclear blood cell. In some embodiments, the compound delivered to the immune cell can include a chemical compound, a micro-RNA, or a micro-RNA mimic.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

FIG. 3C illustrates a pairing scheme for a portion of the WNT10B RNA and the miRNA miR-7113-5p in accordance with an embodiment of the disclosure. FIG. 3C discloses SEQ ID NOs. 1-2, respectively, in order of appearance.

FIG. 3D illustrates a plot displaying RE of miR-7113-5p for cells extracted from patients having PTSD and cells from controls in accordance with embodiments of the disclosure.

FIG. 3E illustrates a bar graph displaying RE WNT10B under different conditions in accordance with embodiments of the disclosure.

FIG. 3F illustrates a gel displaying protein expression for WNT10B and GAPDH under conditions that include a scrambled, an inhibitor, or a mimic miRNA in accordance with embodiments of the disclosure.

Figure 1A:
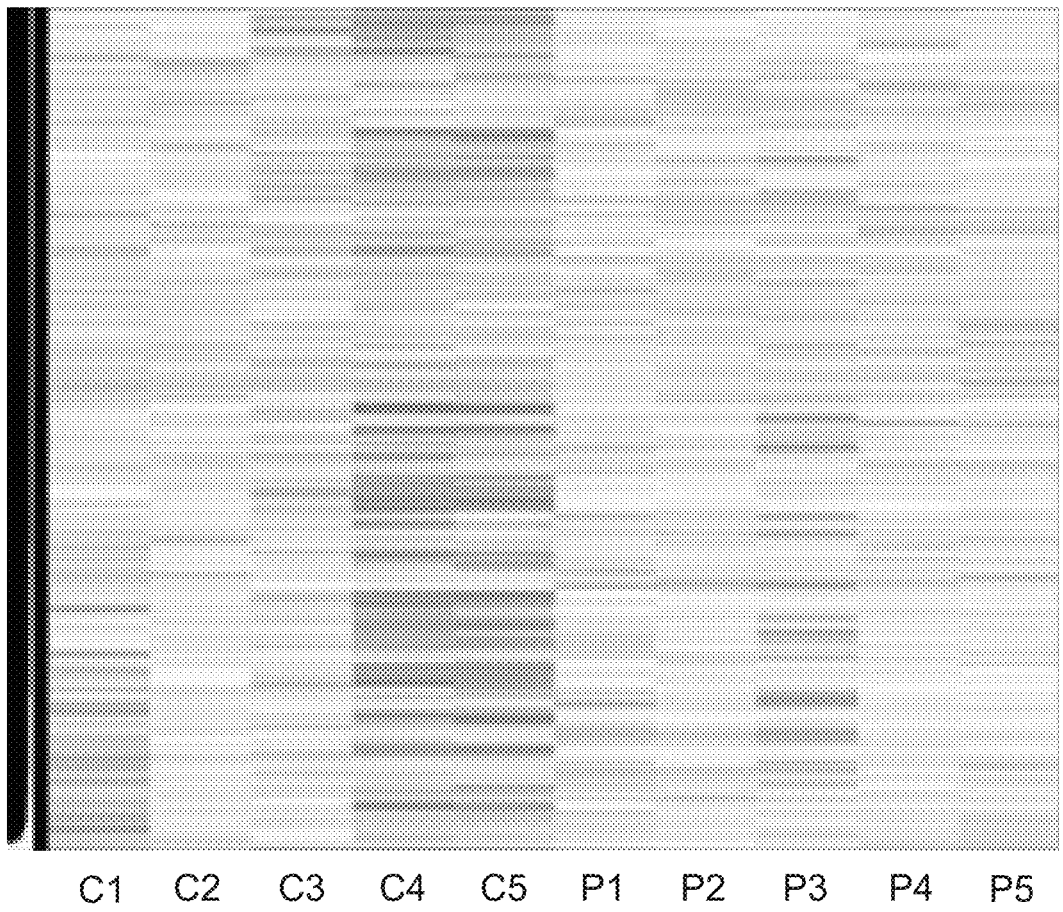
FIG. 1A illustrates example data from RNA-seq analyses in accordance with embodiments of the disclosure.

Repeat use of reference characters in the present specification and drawings is intended to represent the same or analogous features or elements of the present invention. In some instances, multiple notations can be used in the figures to represent the same compound or gene. For example, the cytokine and/or the gene encoding interferon gamma can be referenced using either IFNγ or IFNG both in the Drawings and in this disclosure including the claims. Other cytokines and their corresponding genes are represented using standard nomenclature. For example, the class of interleukins can be represented as IL followed by the representative number (e.g., interleukin 17 can be represented as IL-17.)

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only and is not intended as limiting the broader aspects of the present invention, which broader aspects are embodied exemplary constructions.

Generally, the present disclosure is directed to compositions and methods to treat the inflammatory response present in certain diseases and illnesses by modifying a dysregulation of one or more genes associated with the wnt-signaling pathway. Embodiments of the disclosure can provide methods for treating an inflammatory response in a patient by identifying the inflammatory response and modifying the inflammatory response.

In an embodiment, identifying the inflammatory response can include isolating a peripheral blood mononuclear cell (PBMC) from the patient, measuring an expression of at least one gene or an expression of at least one protein in the wnt-signaling pathway in the peripheral blood mononuclear cell and comparing the expression level to a population expression level. As an example, a PBMC can be isolated from a patient and gene expression can be determined using quantitative real-time polymerase chain reaction (qRT-PCR). In addition, or alternatively, protein expression can be determined using a western blot assay. Other methods for determining gene expression and protein expression can be practiced with embodiments of the disclosure, thus determining gene expression is not limited only to qRT-PCR and determining protein expression is not limited only to western blot.

In addition, or alternatively, identifying the inflammatory response can include isolating a peripheral blood mononuclear cell (PBMC) from the patient, measuring an expression of at least one micro-RNA in the peripheral blood mononuclear cell (e.g., a micro-RNA identified in FIG. 3B) and comparing the micro-RNA expression level to a population expression level.

In some embodiments, identifying the inflammatory response can further include comparing the expression level of the at least one gene or the expression level of the at least one protein to a population expression level. Generally, the population expression level can define a protein expression, a gene expression, and/or a micro-RNA expression determined from a control population. The control population can include a person or persons that have not been diagnosed with an inflammatory condition or disease, such as PTSD, irritable bowel syndrome, or arthritis. In some embodiments, the control population can include only persons that have not been diagnosed with an inflammatory condition or disease. In other embodiments, the control population can include a majority of persons (e.g., >50%) that have not been diagnosed with an inflammatory condition.

Additionally, different types of comparisons can include percentiles, statistical significance, greater than, less than, or combinations thereof. As an example, a student's t-test could be used to determine whether the expression of the at least one gene or the expression of the at least one protein is upregulated or downregulated on a statistically significant basis when compared to the population expression level for the gene or protein in wnt-signaling pathway (e.g., the determined p-value is less than a threshold). In some embodiments, the statistical significance may also incorporate a disease prevalence, such as the rate of an inflammatory diseased in a population (e.g., cases of PTSD in the U.S. per capita or percentage of PTSD in Veterans). For these embodiments, identifying the inflammatory response can include assessing the patient's medical history or background.

Figure 3A:
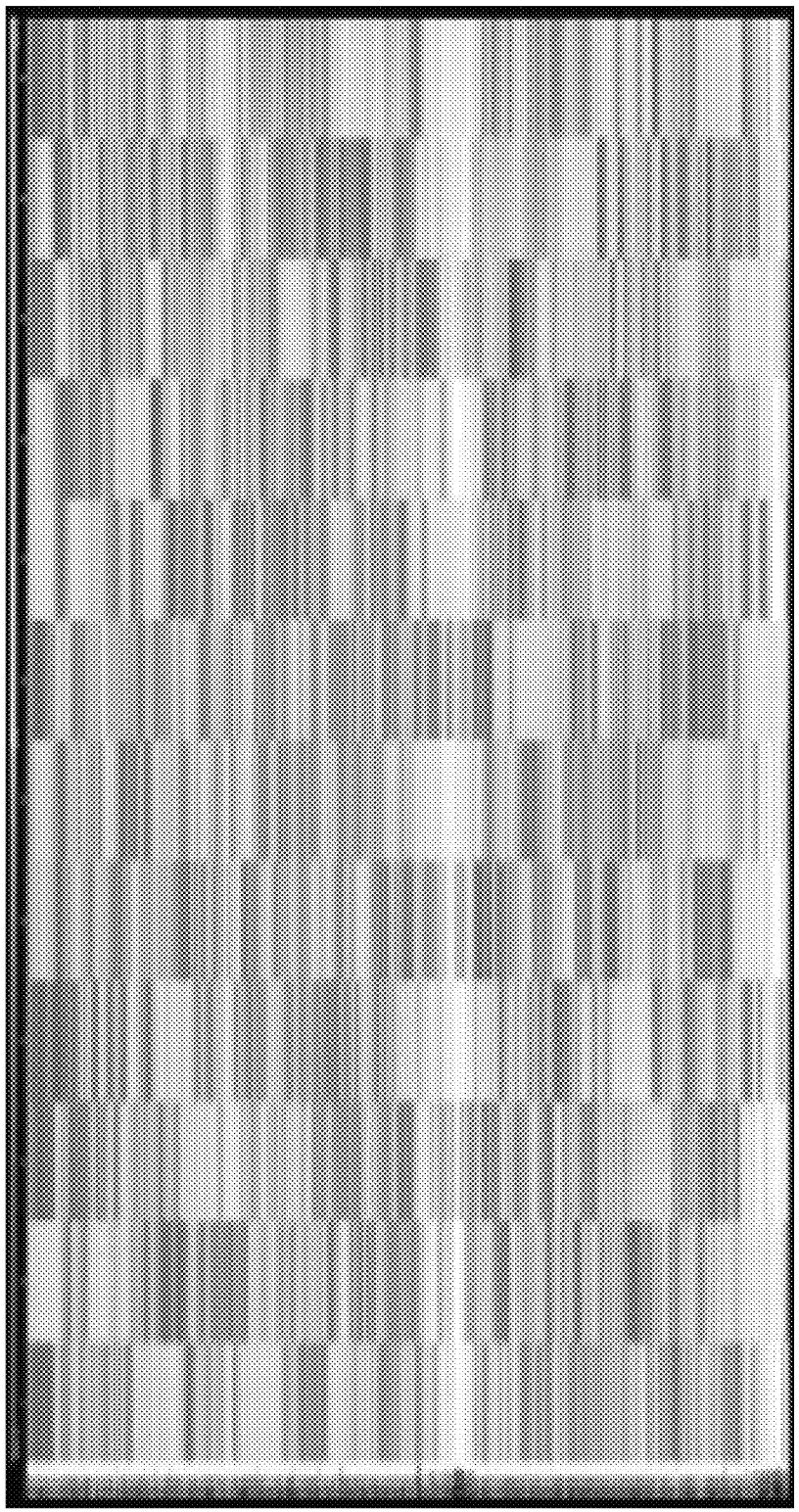
FIG. 3A illustrates example data from micro-RNA (miRNA) expression analysis for cells extracted from patients having PTSD (P1-P6) and cells extracted from controls (C1-C6) in accordance with embodiments of the disclosure.
Figure 3B:
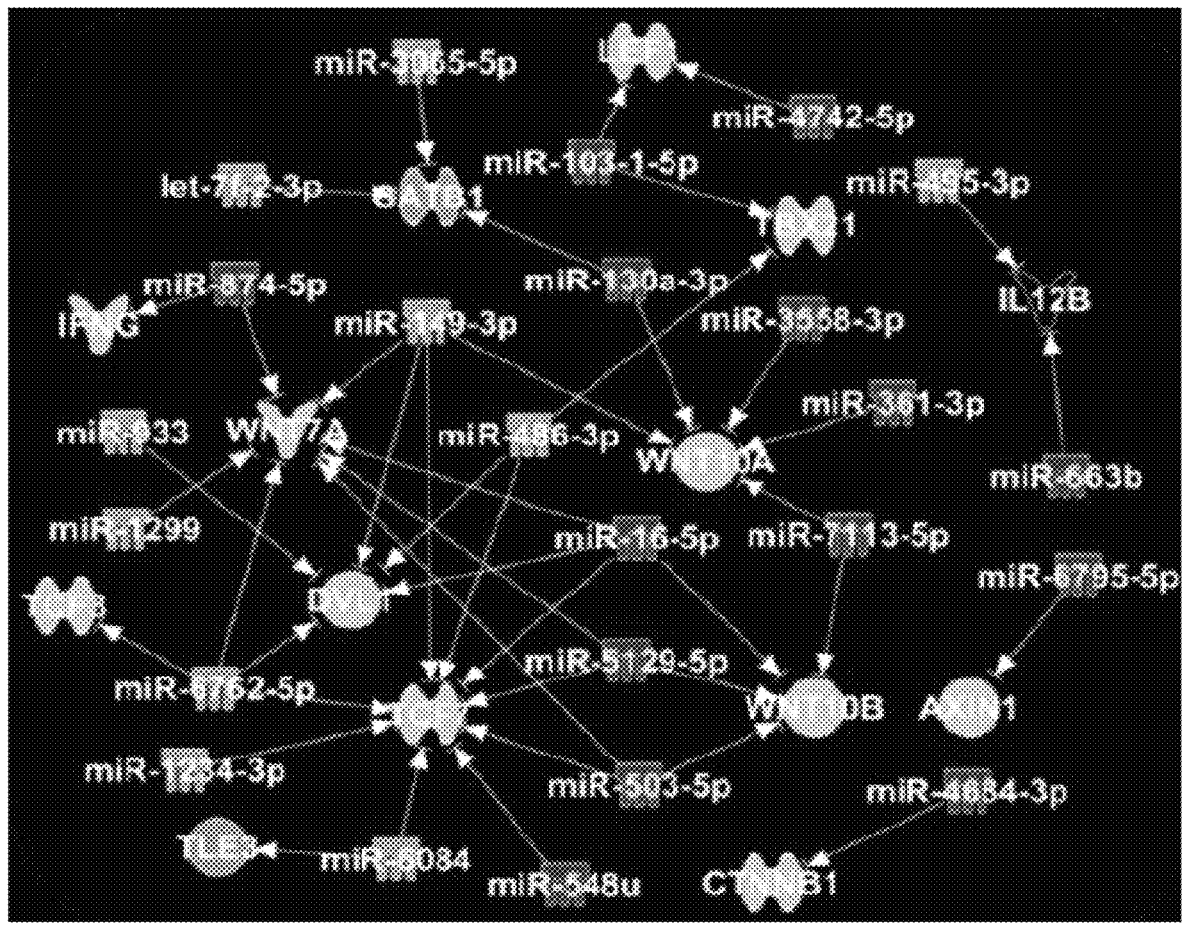
FIG. 3B illustrates a map of genes associated with the wnt-signaling pathway, and miRNAs targeting the genes. RNA expression or miRNA expression is illustrated relative to whether gene expression or miRNA is upregulated in cells extracted from PTSD patients (light gray) or downregulated (dark gray) in accordance with an embodiment of the disclosure.
Figure 4A:
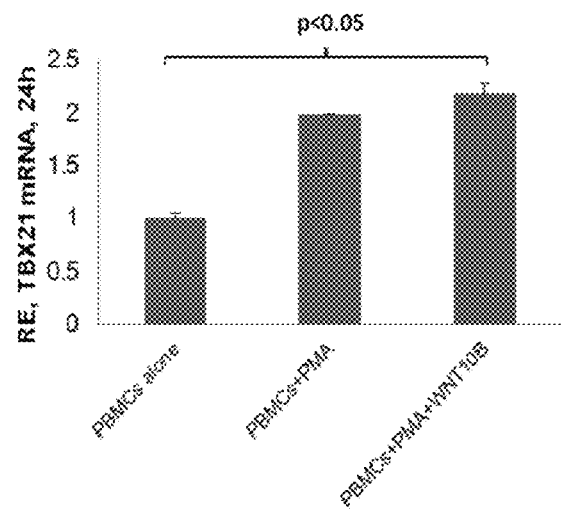
FIG. 4A illustrates a bar graph displaying example data for RE of TBX21 mRNA after 24 hours for PBMCs under conditions including: alone, +PMA, +PMA+WNT10B.
Figure 4B:
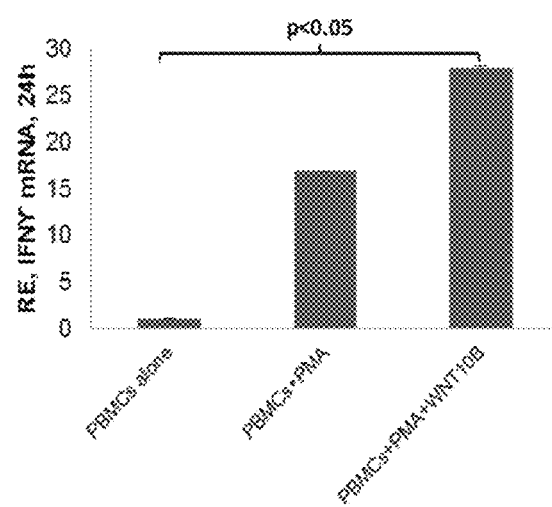
FIG. 4B illustrates a bar graph displaying example data for RE of IFNγ mRNA after 24 hours for PBMCs under conditions including: alone, +PMA, +PMA+WNT10B.
Figure 4C:
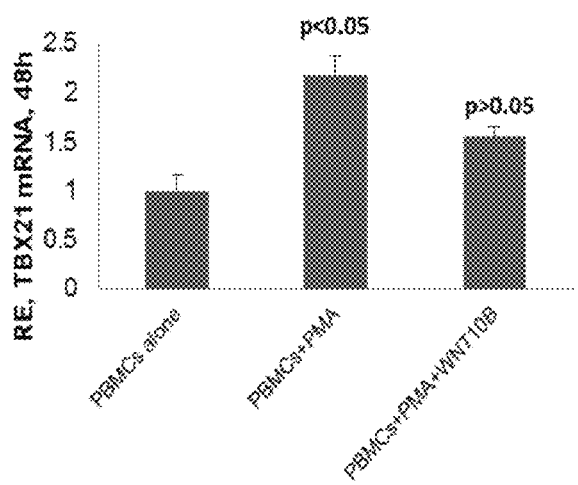
FIG. 4C illustrates a bar graph displaying example data for RE of TBX21 mRNA after 48 hours for PBMCs under conditions including: alone, +PMA, +PMA+WNT10B.
Figure 4D:
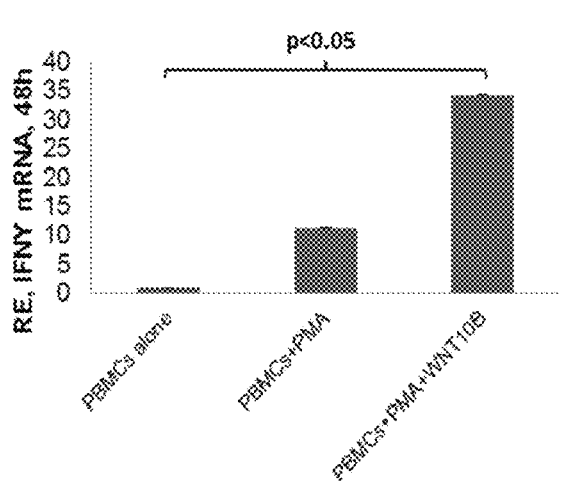
FIG. 4D illustrates a bar graph displaying example data for RE of IFNγ mRNA after 48 hours for PBMCs under conditions including: alone, +PMA, +PMA+WNT10B.
Figure 4E:
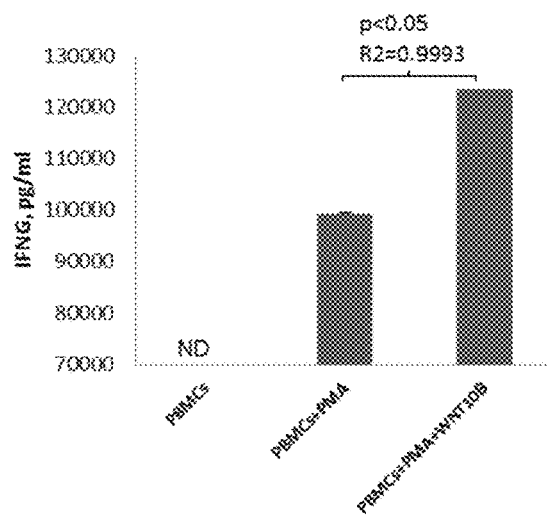
FIG. 4E illustrates a bar graph displaying example data for RE of IFNG in pg/ml for PBMCs under conditions including alone, +PMA, +PMA+WNT10B.
Figure 4F:
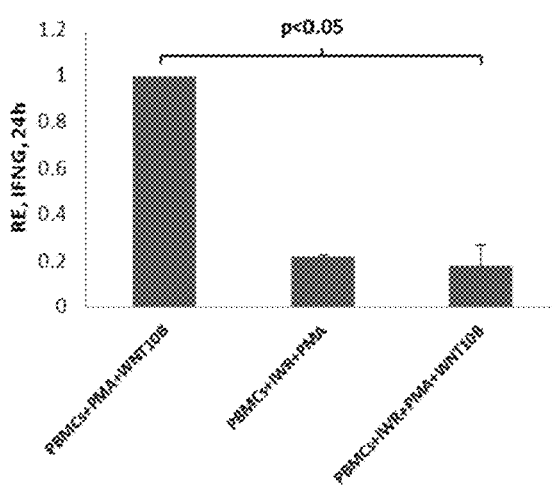
FIG. 4F illustrates a bar graph displaying example data for RE of IFNG after 24 hours for PBMCs under conditions including +PMA+WNT10B, +IWR+PMA, and +IWR+PMS+WNT 10B.
Figure 4G:
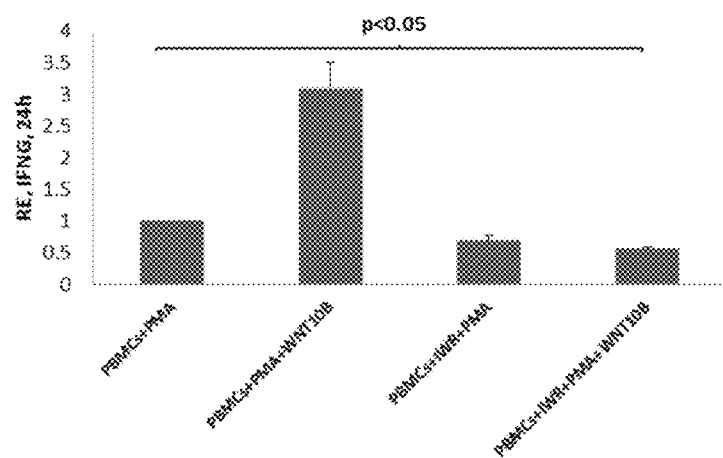
FIG. 4G illustrates a bar graph displaying example data for RE of IFNG after 24 hours for PBMCs under conditions including +PMA, +PMA+WNT 10B, +IWR+PMA, and +IWR+PMA+WNT 10B
Figure 5A:
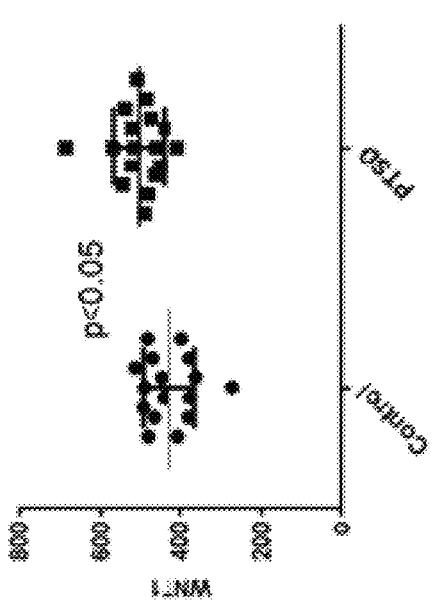
FIG. 5A illustrates a plot displaying example data for the expression of WNT10B in accordance with embodiments of the disclosure.
Figure 5B:
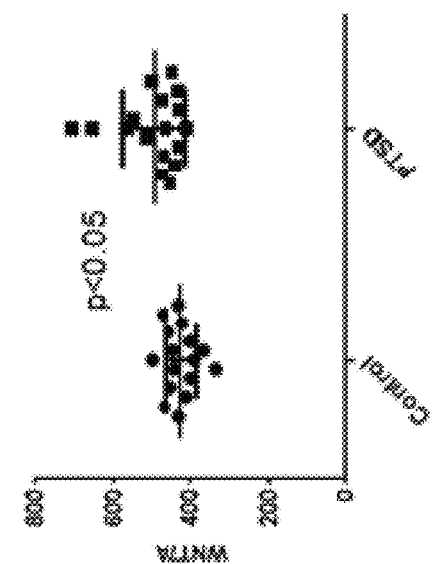
FIG. 5B illustrates a plot displaying example data for the expression of WNT7A in accordance with embodiments of the disclosure.
Figure 5C:
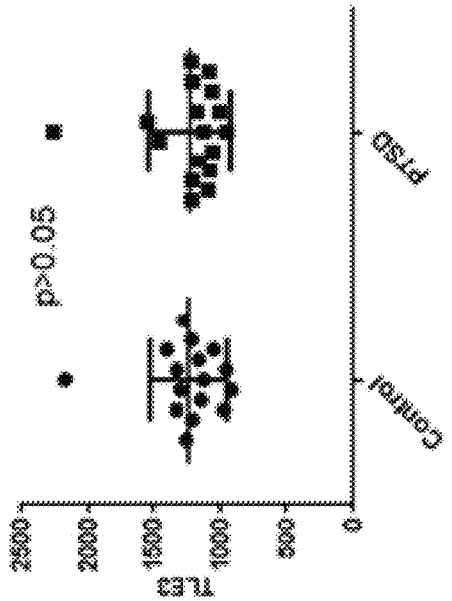
FIG. 5C illustrates a plot displaying example data for the expression of WNT1 in accordance with embodiments of the disclosure.
Figure 5D:
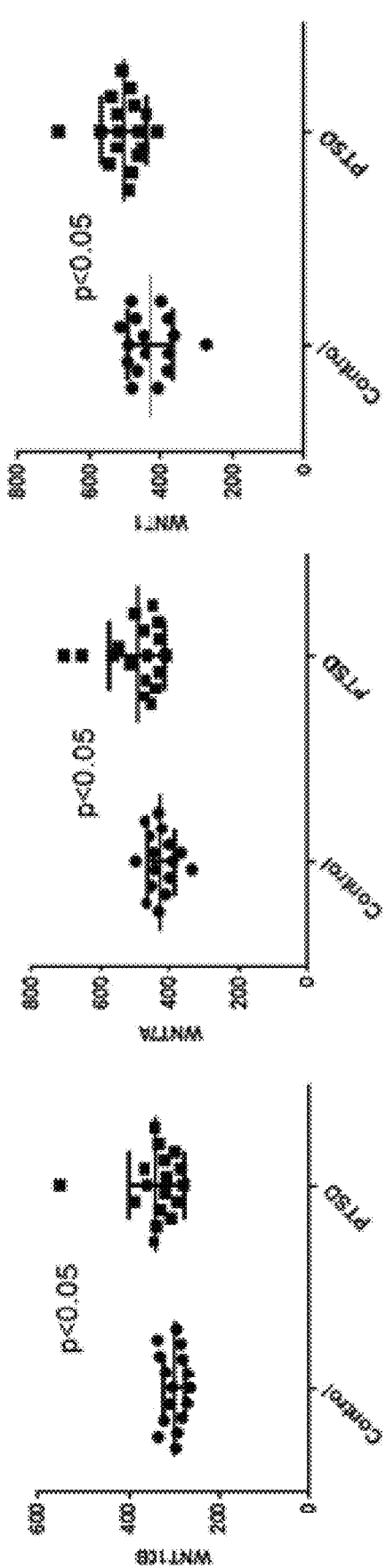
FIG. 5D illustrates a plot displaying example data for the expression of TCF7 in accordance with embodiments of the disclosure.
Figure 5E:
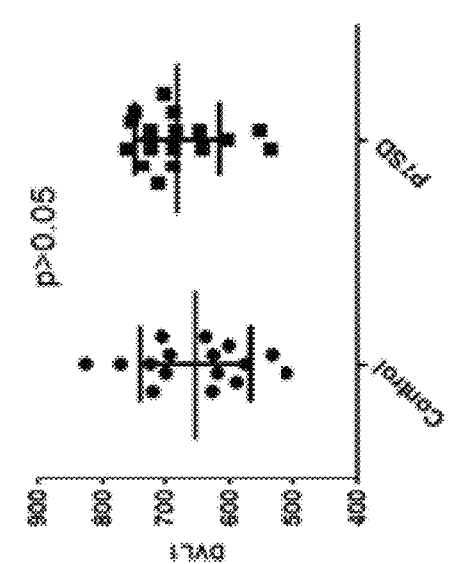
FIG. 5E illustrates a plot displaying example data for the expression of DVL1 in accordance with embodiments of the disclosure.
Figure 5F:
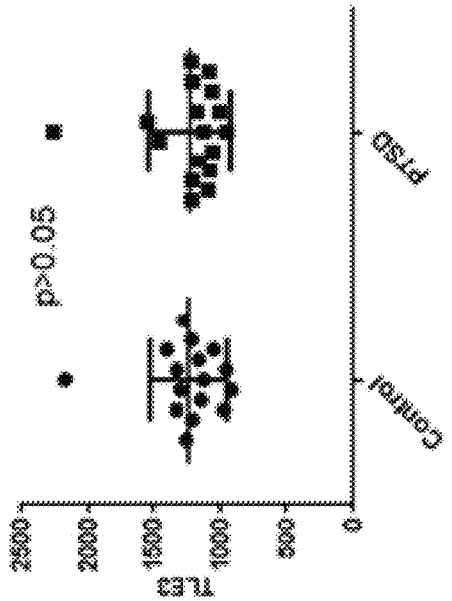
FIG. 5F illustrates a plot displaying example data for the expression of TLE3 in accordance with embodiments of the disclosure.
Figure 6:
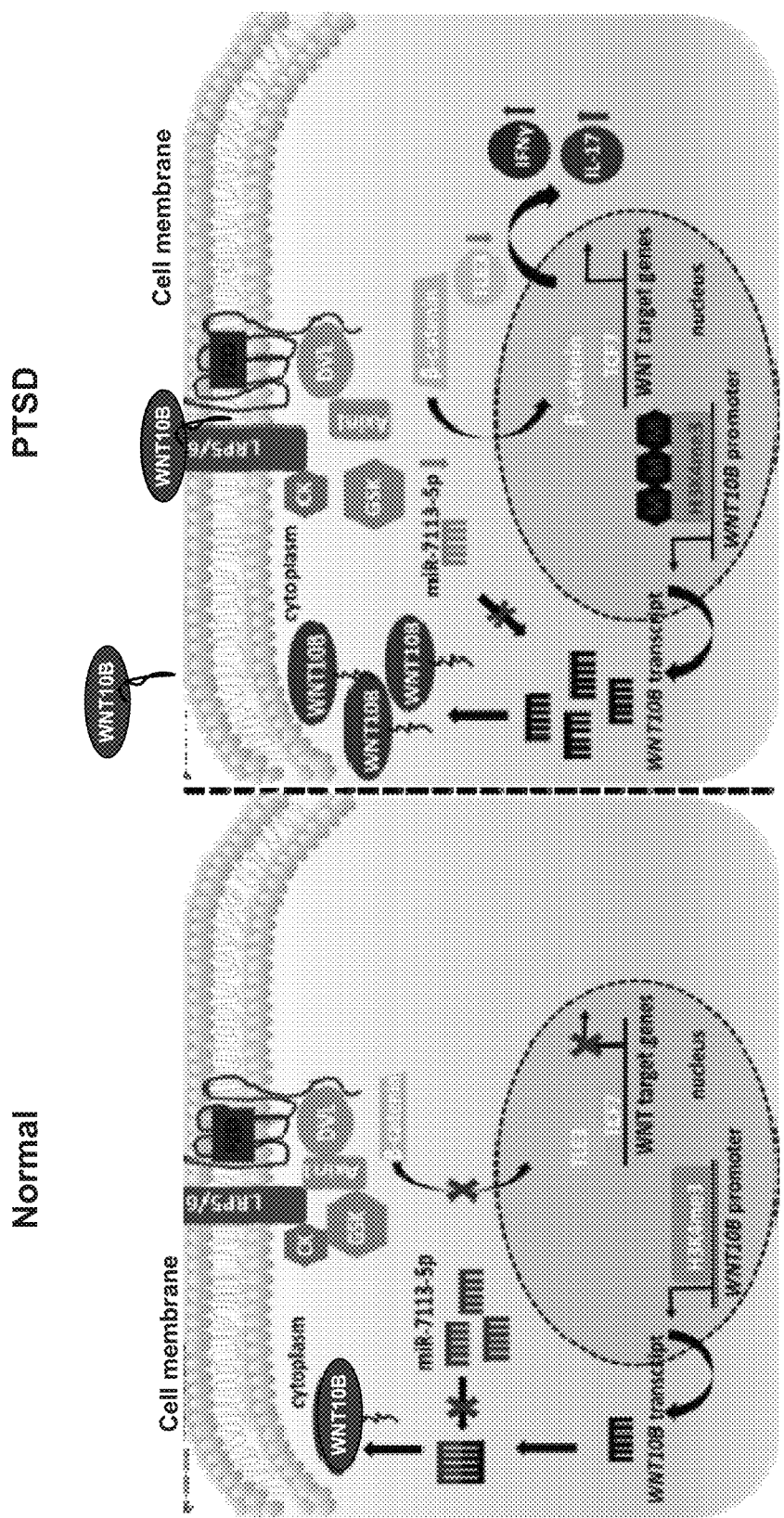
FIG. 6 illustrates a portion of the wnt-signaling pathway shown for a normal cell and a dysregulated (PTSD) cell.

For embodiments of the disclosure, the wnt-signaling pathway includes proteins, genes, and micro-RNA associated with the network shown in FIG. 3B which includes the genes: WNT1, WNT10B, WNT10A, WNT7A, DVL1, TCF7, IFNγ, TLE3 and CTNNB 1. The genes shown correspond to the proteins: Wnt-1, Wnt-10b, Wnt-10a, Wnt-7a, DVL-1, TCF-7, interferon gamma (IFNγ or IFNG), transducin-like enhancer protein (TLE-3) and beta-catenin (CTNNB-1). The micro-RNA shown correspond to miRNA: miR-3065-5p, miR-103-1-5p, miR-874-5p, miR-149-3p, miR-130a-3p, miR-4742-5p, miR-495-3p, miR-3558-3p, miR-361-3p, miR-933, miR-486-3p, miR-1299, miR-16-5p, miR-6762-5p, miR-5129-5p, miR-1234-3p, miR-503-5p, miR-6084, miR-548u, miR-663b, miR-7113-5p, miR-6795-5p, and miR-4684-3p. In example embodiments of the disclosure, at least one gene and/or at least one protein included in the wnt-signaling pathway can be used to measure the gene expression (e.g., expression of WNT10B), the protein expression (e.g., Wnt-10b), and/or the miRNA expression (e.g., expression of miR-7113-5p) from the PBMC isolated from the patient. Further, the patient expression can be compared to a population expression for at least the same gene or the same protein to determine if expression is increased or decreased.

Generally, the RNA sequences associated with the miRNA described herein can be found using a search database (e.g., Targetscan, miRBase.) For example, miR-7113-5p has the oligonucleotide sequence UCCAGGGAGACAGUGUGUGAG (SEQ ID NO: 2).

In a non-limiting example embodiment, a PBMC can be isolated from a patient. The expression of the WNT 10B gene can be determined for the patient PBMC using a method such as qRT-PCR and this result can be compared to a control expression level for the gene from PBMC. Utilizing this information, the inflammatory response can be modified. As an example, modifying the inflammatory response can be based, at least in part, on the comparison of the expression of WNT10B in the patient versus control expression level of WNT10B. Example methods for modifying the inflammatory response may include compounds that can modify the wnt-signaling pathway and/or the immune system (e.g., miRNA, WNT signaling inhibitors, siRNA, NSAIDs, and steroids.)

In embodiments of the disclosure, modifying the inflammatory response can include delivering a compound to the patient. In certain embodiments, the compound can include one or more of the following micro RNA: miR-7113-5p, miR-503-5p, miR-5129-5p, miR-16-5p, miR-6795-5p, miR-4684-3p, miR-361-3p, miR-3558-3p, miR-874-5p, and combinations thereof.

In some embodiments, modifying the inflammatory response can include delivering a compound that includes a micro RNA mimic to the patient. The miRNA mimic can include a structure or structures similar to one or more of the following miRNA: miR-7113-5p, miR-503-5p, miR-5129-5p, miR-16-5p, miR-6795-5p, miR-4684-3p, miR-361-3p, miR-3558-3p, and miR-874-5p. Development and/or structures for the miRNA mimics can include an artificially synthesized RNA sequence that differs in at least one base pair so that the mimic is only partially complementary to the target sequence. Alternative structures for the miRNA mimics can include substituting uracil bases in the miRNA structure for thiamine bases in the mimic structure. Additional modifications to the miRNA structure that can be used to produce a miRNA mimic can include alkylating (e.g., methylation) one or more hydroxyl groups and/or one or more amine groups of the miRNA structure.

In some embodiments, the delivering the miRNA or miRNA mimic to the patient can include delivering a precursor for processing within the cell. For example, the precursor could include an expression vector encoding a sequence for expressing the miRNA (e.g., miR-7113-5p) or the miRNA mimic. In an embodiment, miR-7113-5p may be utilized in conjunction with a suitable expression system, and a quantity of miR-7113-5p nucleic acids can be generated from such expression systems. Recombinant expression is usefully accomplished using a vector, such as a plasmid. The vector can include a promoter operably linked to nucleic acid encoding a miR-7113-5p nucleic acid. The vector can also include other elements required for transcription and translation. As used herein, vector refers to any carrier containing exogenous DNA. Thus, vectors are agents that transport the exogenous nucleic acid into a cell without degradation and include a promoter yielding expression of the nucleic acid in the cells into which it is delivered. Vectors include, but are not limited to, plasmids, viral nucleic acids, viruses, phage nucleic acids, phages, cosmids, and artificial chromosomes. A variety of prokaryotic and eukaryotic expression vectors suitable for carrying, encoding and/or expressing miR-7113-5p nucleic acids are encompassed herein. Such expression vectors include, for example, pET, pET3d, pCR2.1, pBAD, pUC, and yeast vectors.

A variety of regulatory elements can be included in an expression cassette and/or expression vector, including promoters, enhancers, translational initiation sequences, transcription termination sequences, and other elements.

The expression of miR-7113-5p from an expression cassette or expression vector can be controlled by any promoter capable of expression in prokaryotic cells or eukaryotic cells. Examples of prokaryotic promoters that can be used include, but are not limited to, SP6, T7, T5, tac, bla, trp, gal, lac, or maltose promoters. Examples of eukaryotic promoters that can be used include, but are not limited to, constitutive promoters, e.g., viral promoters such as CMV, SV40 and RSV promoters, as well as regulatable promoters, e.g., an inducible or repressible promoter such as the tet promoter, the hsp70 promoter, and a synthetic promoter regulated by CRE. Vectors for bacterial expression include pGEX-5X-3, and for eukaryotic expression, include pCIneo-CMV.

In certain embodiments, modifying the inflammatory response can be based in part on the dysfunction identified in the wnt-signaling pathway. As an example embodiment, the dysfunction can include an increase in gene expression for WNT10B or in the Wnt-10b protein and modifying the inflammatory response can include delivering a compound that includes a micro-RNA or a micro-RNA mimic selected from the group: miR-7113-5p, miR-503-5p, miR-5129-5p, miR-16-5p, and combinations thereof.

As another example embodiment, the comparison described previously can provide information concerning a statistically significant increase in gene expression for WNT10A or in the Wnt-10a protein and modifying the inflammatory response can include delivering a compound that includes a micro-RNA or a micro-RNA mimic selected from the group: miR-130a-3p, miR-3558-3p, miR-361-3p, miR-7113-5p, and combinations thereof.

As another example embodiment, the comparison described previously can provide information concerning a statistically significant increase in gene expression for WNT7A or in the Wnt-7a protein and modifying the inflammatory response can include delivering a compound that includes a micro-RNA or a micro-RNA mimic selected from the group: miR-874-5p, miR-16-5p, miR-5129-5p, miR-503-5p, and combinations thereof.

As another example embodiment, the comparison described previously can provide information concerning a statistically significant increase in gene expression for DVL1 or in the DVL-1 protein and modifying the inflammatory response can include delivering a compound that includes a micro-RNA or a micro-RNA mimic of miR-16-5p.

As another example embodiment, the comparison described previously can provide information concerning a statistically significant increase in gene expression for TCF7 or in the TCF-7 protein and modifying the inflammatory response can include delivering a compound that includes a micro-RNA or a micro-RNA mimic selected from the group: miR-548u, miR-503-5p, miR-5129-5p, and miR-16-5p.

In some embodiments, the comparison described previously can provide information concerning a statistically significant increase in miRNA expression. For these embodiments, modifying the inflammatory response can include delivering a miRNA inhibitor such as a complementary strand to the miRNA or a chemical compound that can inhibit the wnt-signaling pathway.

In an embodiment, the method for treating an inflammatory response in a patient can include identifying a patient diagnosed with an inflammatory disorder and modifying the inflammatory response by delivering a compound or compounds that target one or more genes in the wnt-signaling pathway. In this manner, certain embodiments of the disclosure can be used in combination with other diagnostic procedures to identify an inflammatory disorder or immune system condition (e.g., blood tests including white cell counts and/or cytokine assays). For some patients and doctors, this combination could be used to create personalized treatments or to clarify current treatment options. A non-limiting list of inflammatory disorders and diseases can include: PTSD, obesity, cancer, bacterial infection, rheumatoid arthritis, chronic ulcerative colitis, periodontitis, asthma, and chronic obstructive pulmonary disease.

For embodiments of the disclosure, methods for delivering a compound to a patient can include an administration route selected from intravenous, oral, rectal, nasal, intramuscular, and transdermal. Additionally, or alternatively, in certain embodiments, delivering the compound to the patient can include isolating a blood sample from the patient containing one or more peripheral blood mononuclear cells. Concentrating and/or separating the peripheral blood mononuclear cells from the blood sample (e.g., through centrifugation). Exposing the peripheral blood mononuclear cells to a micro-RNA or a micro-RNA mimic from the group: miR-7113-5p, miR-503-5p, miR-5129-5p, miR-16-5p, miR-6795-5p, miR-4684-3p, miR-361-3p, miR-3558-3p, miR-874-5p, and combinations thereof. And returning a portion of the peripheral blood mononuclear cells to the patient.

Alternatively, or additionally, modifying the inflammatory response can include delivering a chemical compound (e.g., a WNT signaling inhibitor and/or an immune suppressor) to the patient. As an example embodiment, the chemical compound can include 4-(1,3,3a,4,7,7a-Hexahydro-1,3-dioxo-4,7-methano-2H-isoindol-2-yl)-N-8-quinolinyl-benzamide (also known as IWR-1) or a variant of the chemical structure. In some implementations, the chemical compound can include a steroid (e.g., a corticosteroid such as prednisone or dexamethasone), an NSAID (e.g., naproxen or aspirin), a chemotherapeutic (e.g., methotrexate), and/or an antibody.

For embodiments of the disclosure that include delivering more than one compound to the patient (e.g., a miRNA and a chemical compound), delivering the two or more compounds can occur concurrently or substantially concurrently, such as by administering the two or more compounds at the same time. In some embodiments, delivering one of the two or more compounds to the patient can take place in an order (e.g., administering the miRNA followed by administering the chemical compound).

In an example embodiment of the disclosure, modifying the inflammatory response can include delivering at least two compounds to the patient. The at least two compounds can include a miRNA and a chemical compound to modify the dysregulation of the wnt-signaling pathway. As an example, the chemical compound can include 4-(1,3,3a,4,7,7a-Hexahydro-1,3-dioxo-4,7-methano-2H-isoindol-2-yl)-N-8-quinolinyl-benzamide (IWR1), and the miRNA can include miR-7113-5p.

Figure 1B:
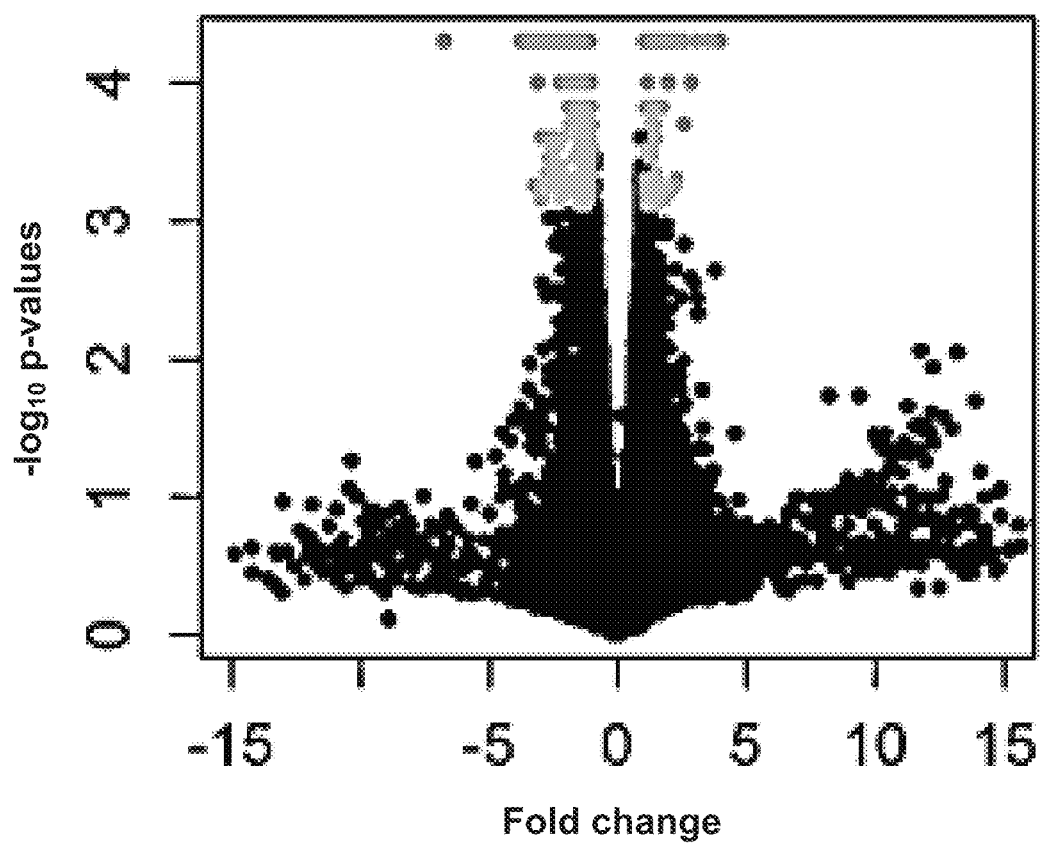
FIG. 1B illustrates example data displaying p-values versus fold change in accordance with an exemplary embodiment of the disclosure.

These embodiments may be better understood in relation to the Figures. For example, FIG. 1A illustrates a heat map of the RNA-seq data from control (C1-C5) and PTSD (P1-P5) samples. In FIG. 1A, genes that are upregulated are shown in light gray and genes that are downregulated are shown in dark gray. FIG. 1B illustrates a volcano plot comparing expression levels of genes in PTSD as fold change (x-axis) against p values (y-axis). Each dot represents a gene and gray dots represent significantly dysregulated genes. Down-regulated genes display a negative value, up-regulated genes display a positive value.

Figure 1C:
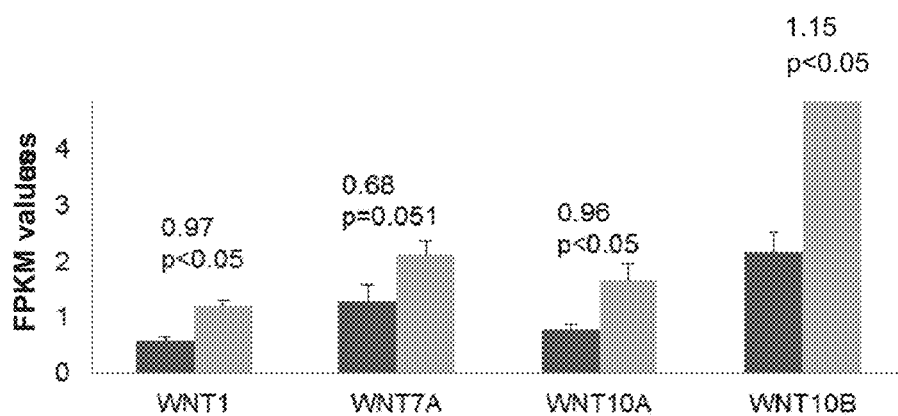
FIG. 1C illustrates a bar graph displaying FPKM values for genes including WNT1, WNT7A, WNT10A, and WNT10B in accordance with embodiments of the disclosure.

In FIG. 1C, expression levels of genes for wnt ligands: WNT1, WNT7A, WNT10A, and WNT10B are shown as FPKM values for control (black bars) and PTSD samples (gray bars).

Figure 1D:
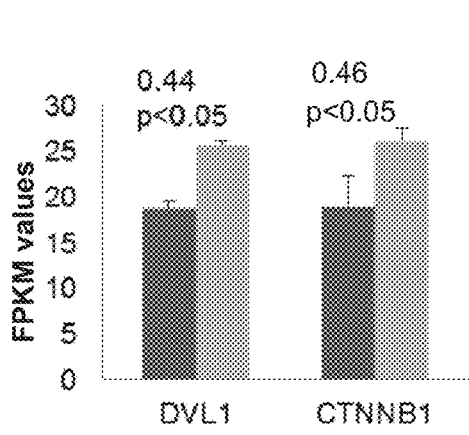
FIG. 1D illustrates a bar graph displaying FPKM values for genes including DVL1 and CTNNB 1 in accordance with embodiments of the disclosure.

In FIG. 1D, expression levels of genes in the wnt-signaling pathway: DVL1 and CTNNB 1 are shown as FPKM values for control (black bars) and PTSD samples (gray bars).

Figure 1E:
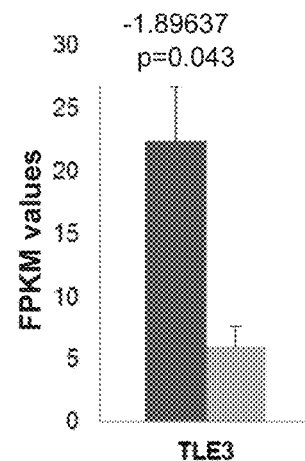
FIG. 1E illustrates a bar graph displaying FPKM values for TLE3 in accordance with embodiments of the disclosure.

In FIG. 1E, expression level of the TLE3 gene in the wnt-signaling pathway is shown as FPKM values for control (black bars) and PTSD samples (gray bars).

Figure 1F:
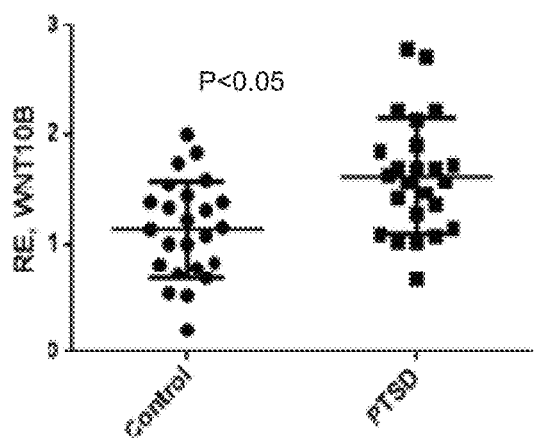
FIG. 1F illustrates a plot displaying relative expression (RE) of WNT10B for control and PTSD samples.

In FIG. 1F, the relative expression (mRNA) is shown comparing the transcript level of WNT 10B and CTNNB 1 to a control using qRT-PCR in 24 control and PTSD samples each.

Figure 2A:
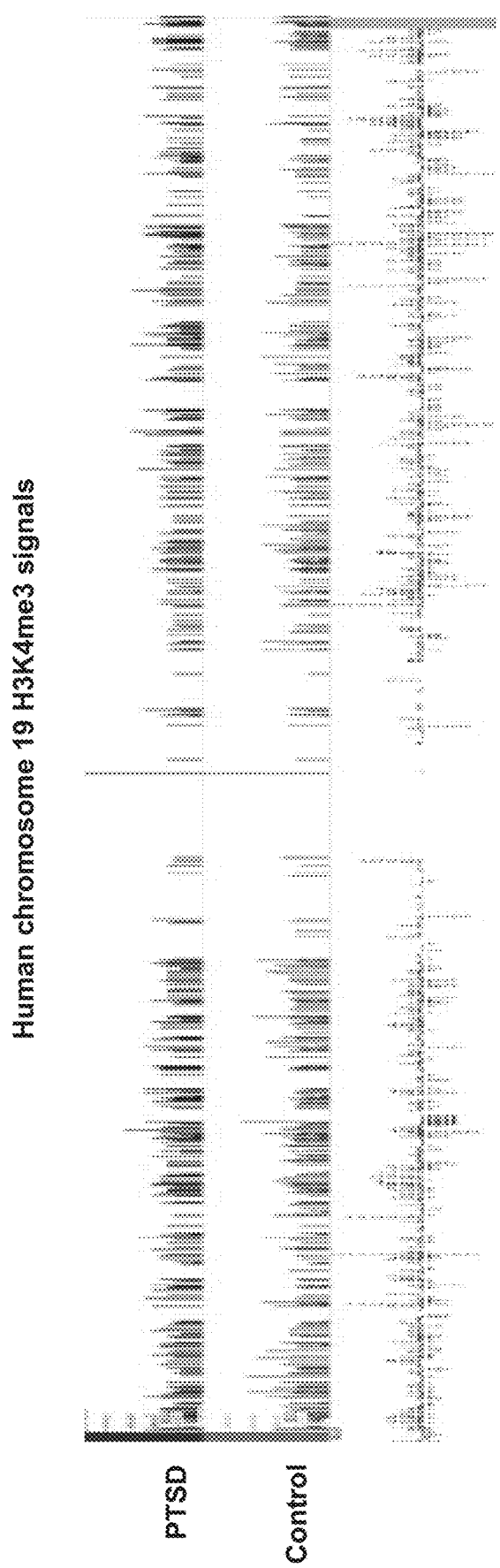
FIG. 2A illustrates example data from a chromatin immunoprecipitation (ChIP) analysis of human chromosome 19 H3K4me3 for PTSD (top) and a control (middle) in accordance with an embodiment of the disclosure.
Figure 2B:
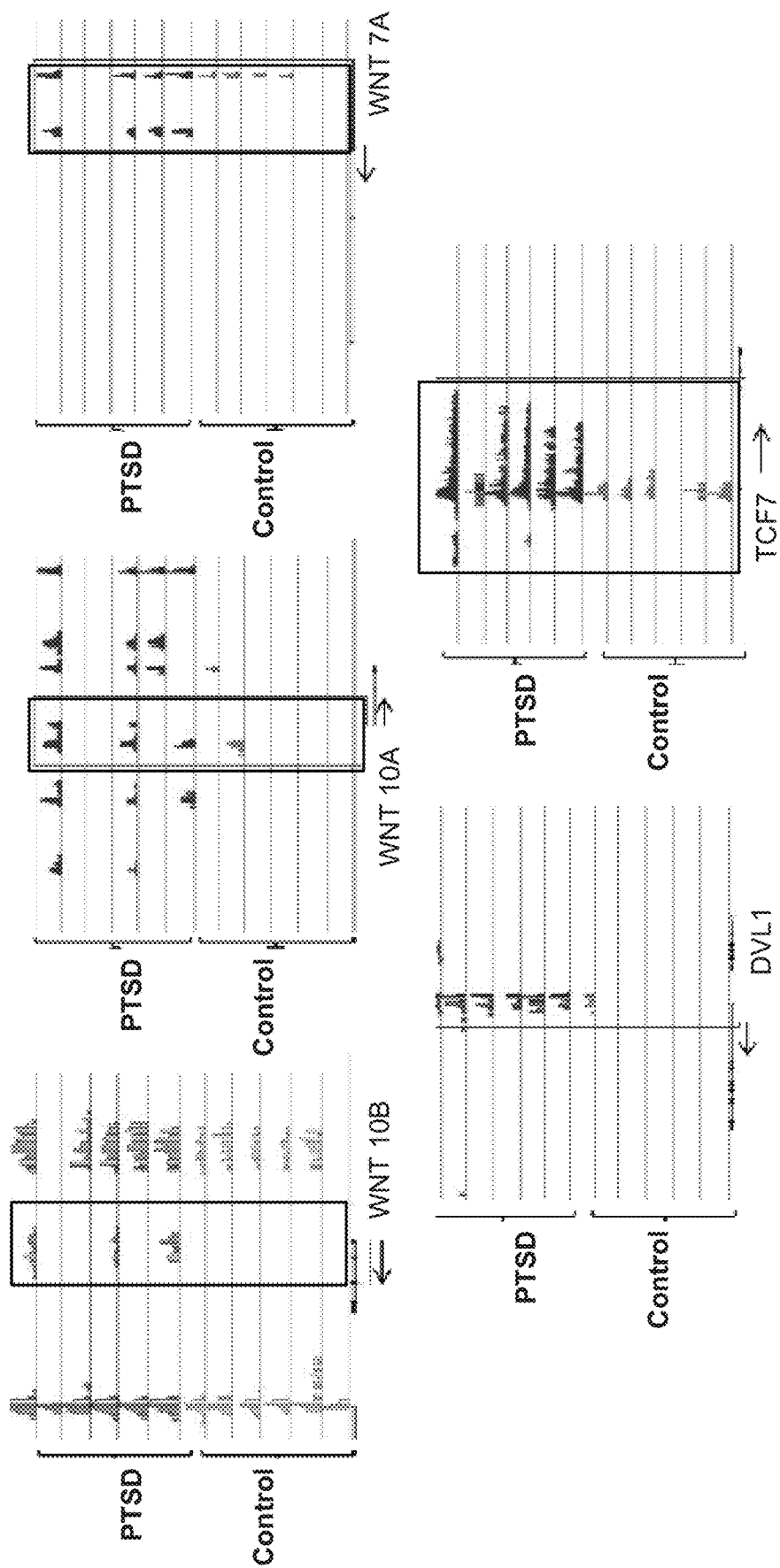
FIG. 2B illustrates regions of FIG. 2A for areas around certain genes that can affect the wnt-signaling pathway in accordance with embodiments of the disclosure; the genes include: WNT10B, WNT10A, WNT7A, DVL1, and TCF7.

FIGS. 2A-2B illustrate data from a ChIP-seq analysis for H3K4me3 from 6 PTSD and 6 control samples. In FIG. 2A, a representative H3K4me3 ChIP-seq signal is shown after visualization of the sequencing data in Integrated Genome Browser (IGB) for human chromosome 19. In FIG. 2B, the H3K4me3 signal around 6 genes associated with the wnt-signaling pathway is shown for 6 controls and 6 PTSD samples. One horizontal line represents a sample and the 6 genes include: WNT10B, WNT10A, WNT7A, DVL1, and TCF7.

Figure 2D:
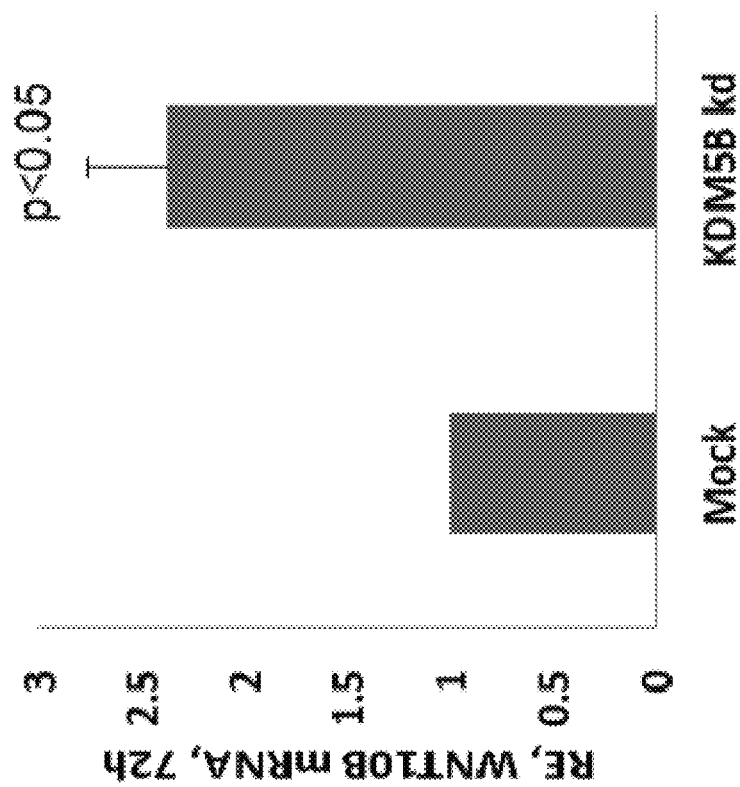
FIG. 2D illustrates a bar graph displaying the RE of WNT10B for mock and knock down of KDM5B in accordance with embodiments of the disclosure.
Figure 2C:
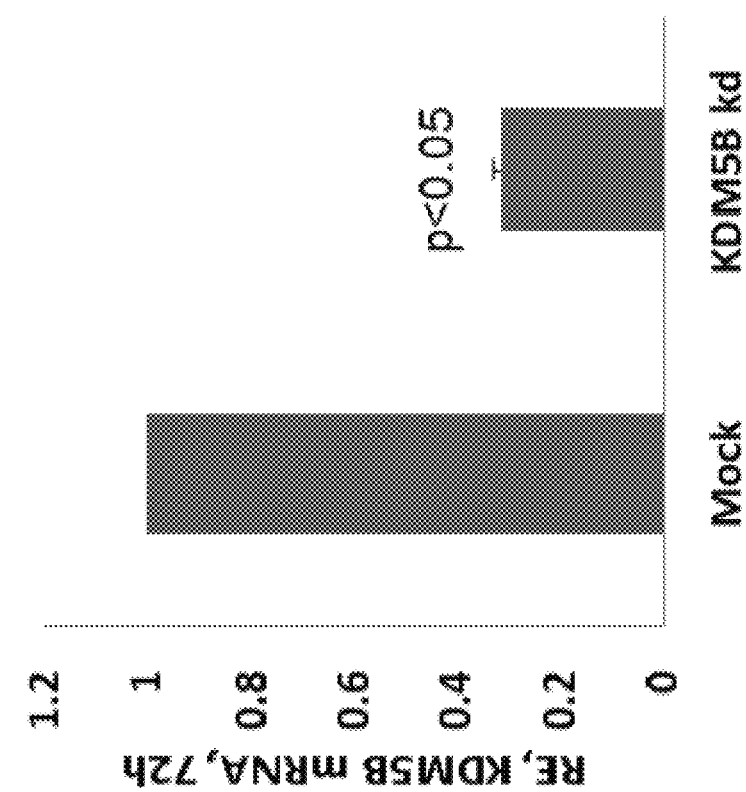
FIG. 2C illustrates a bar graph displaying the RE of KDM5B for mock and knock down (kd) of KDM5B in accordance with embodiments of the disclosure.

FIGS. 2C-2D illustrate bar graphs showing the relative expression (RE) of two genes associated with the wnt-signaling pathway, respectively KDM5B and WNT 10B. The graphs compare expression for a mock (no alteration) against a KDM5B knock down (kd) using siRNA.

In FIG. 3A, a heat map is shown illustrating miRNA expression from control (C1-C6) and PTSD (P1-P6) samples. The heat map is normalized to show upregulated miRNA in light gray and downregulated miRNA in dark gray. In FIG. 3B, some of the data from FIGS. 1A and 3A is mapped using the Ingenuity Pathway Analysis tool, Qiagen. Again, genes or miRNA shown in light gray are upregulated in PTSD samples, and genes or miRNA shown in dark gray are downregulated in PTSD samples.

In FIG. 3C, a nucleotide pairing schema is illustrated for miR-7113-5p and WNT10B 3'UTR obtained from TargetScan.

FIG. 3D illustrates a bar graph showing the relative expression (RE) of miR-7113-5p for control samples and PTSD samples. The graph indicates a statistically significant decrease in miR-7113-5p expression for PTSD samples, using data from 24 controls and PTSD patients each.

FIGS. 3E and 3F illustrate, respectively a bar graph showing the RE of the WNT10B transcript and a western blot gel showing the expression of protein in THP1 cells. In FIG. 3F, protein expression is also shown for a control protein, glyceraldehyde 3-phosphate dehydrogenase (GAPDH.) Data is shown after transfection with scrambled miR-7113-5p, an inhibitor, or a miR-7113-5p mimic.

FIGS. 4A-4G, illustrate bar graphs showing the expression or RE of genes encoding T-box transcription factor (TBX21) or interferon gamma (IFNγ/IFNG) under conditions including PBMCs alone, or in culture with phorbol 12-myristate 13-acetate (PMA) or PMA and WNT10B.

Example 1

Example 1 discusses a study using various methods and procedures. The study supports exemplary embodiments that may be understood in conjunction with the Drawings and Description provided herein.

Methods

Patient Population

Two groups of PTSD patients. One group of PTSD patients consisted of Veterans of either the 1991 Persian Gulf, Iraq, or Afghanistan wars, and the second group consisted of patients from Detroit Neighborhood Health Study (DNHS). All donors were first clinically assessed by professionals for PTSD employing the psychometric properties of the PTSD Checklist (PCL), and the PTSD diagnosis was validated by the Clinician Administered PTSD Scale in addition to the Diagnostic and Statistical Manual of Mental Disorder (DSM-V). Exclusion criteria included current alcohol and other substance abuse, current immunosuppressive drug treatment, or currently being diagnosed with an immunosuppressive disease. The control individuals were age-matched healthy volunteers, who did not have any symptoms of active infection or any history of immune compromise, such as HIV, cancer, pregnancy or on chronic steroid therapy. Twenty-four control and 24 PTSD patients were included in the present study, and the number of samples used in each assay is indicated in the figure legends.

Sample Collection and RNA Isolation

Peripheral blood samples (2-10 ml) collected in EDTA coated collection tubes were processed to isolate PBMCs by density centrifugation using Ficoll-Paque (GE Healthcare, Uppsala, Sweden). Using a universal kit (AllPrep DNA/RNA/miRNA Universal Kit, Qiagen, Valencia, Calif.) recommended for simultaneous isolation of high-quality DNA and total RNA, including miRNAs, all the three entities were isolated from the same PBMCs and immediately frozen at −80° C. until use.

RNA-Sequencing (RNA-Seq)

Five control and 5 PTSD patient samples were analyzed. Libraries were constructed using Illumina TruSeq RNA Sample Preparation kit as described in Bam et al., (2016). Briefly, total RNA from PBMCs was isolated using the Qiagen AllPrep DNA/RNA/miRNA Universal Kit. Following manufacturer instruction, oligo-dT beads were then added to 1 Lg of total RNA to isolate mRNA. The mRNA obtained was fragmented to 200-400 bases. The RNA fragments were then reverse transcribed into double stranded cDNA fragments followed by repairing the DNA fragments to generate blunt ends using T4 DNA polymerase, Klenow polymerase and T4 polynucleotide kinase. The DNA fragments were purified using Qiagen PCR purification kit (Qiagen #28004), following which an "A" base was added to the 3' end of the blunt DNA fragment by Klenow fragment. Using DNA ligase, sequencing adapters were ligated to the ends of DNA fragments. The libraries were then amplified by limited PCR cycles (15 cycles) using primers provided in the kit. The PCR products were gel separated by running in a 2% agarose gel and fragments with sizes ranging from 250 bp to 400 bp were excised and purified using the QiAquick Gel Extraction Kit (Qiagen #28704). The concentration of the libraries was determined by a NanoDrop spectrophotometer (Thermo Scientific, Wilmington, Del.). The library was sequenced by Illumina HiSeq 2000 at Tufts University Genomic core facility. Raw sequencing reads (50 bp single-end) were mapped to human genome build hg19 using Tophat 2. The accepted hits were used for assembling transcripts and estimating their abundance using Cufflinks. The differentially expressed gene, promoter usage and splicing forms were determined by Cuffdiff and Cuffcompare.

Chromatin Immunoprecipitation Sequencing (ChIP-Seq)

Samples were obtained from the Detroit Neighborhood Health Study (DNHS) collection. For chromatin and library preparation from as low as 10,000 cells, the following kits from Diagenode (Diagenode Inc. NJ, USA) were used: True MicroChIP & MicroPlex Library Preparation™ Package (cat #C01010131) and MicroPlex Library Preparation Kit v2 (cat #C05010014). Following the instructions of the kit manufacturer, PBMCs (20-40×10³ cells) from both controls and PTSD patients were treated with 27 µl of 36.5% formaldehyde to cross link histone and DNA. The mixture was incubated for 10 minutes at room temperature with gentle shaking. To quench the formaldehyde, 115 µl of 10X glycine was added and incubated further for 5 minutes at room temperature. Cells were then pelleted and washed with cold PBS for 2 times. Nuclear membrane disruption and chromatin shearing was achieved in lysis buffer solution by sonicating the samples at 4° C. in a temperature-controlled Bioruptor sonicator (Diagenode Inc.) following manufacturer instructions. Sample was centrifuged at 13,000 rpm for 10 minutes, and the supernatant was used for chromatin immunoprecipitation (ChIP) with antibody against human H3K4me3 from Diagenode Inc. (cat #C15410003-50). After overnight incubation period at 4° C. with gentle rotation, protein G beads were added and incubated further for 2 hours. The protein G bead bound antibody with chromatin was separated from the solution by applying magnetic force, washed three times with low salt wash buffer and once with high salt wash buffer. Each wash lasted for 5 minutes with gentle rotation at 4° C. Chromatin was re-suspended in elution buffer and the cross link was reversed by treating the immunoprecipitated chromatin with proteinase K at 65° C. for 45 minutes with constant vortexing. Size selection of the fragments was performed using SPRI beads (cat #B23317) from Beckman Coulter. DNA fragments of desired size were then re-suspended in water and quantified. The sequencing library was constructed using MicroPlex Library Preparation Kit v2 (cat #C05010014, Diagenode Inc.) according to the manufacturer's instruction and sequenced by Illumina NextSeq500 at University of South Carolina School of Medicine.

Micro-RNA Microarray

The microarray included 6 controls (C1-C6) and 6 PTSD patients (P1-P6). The included samples were from the DNHS collection. Total RNA, including mRNA, miRNA, and other small RNA molecules, were isolated from PBMC samples as described previously. Total RNA samples were then used in the analysis of miRNA dysregulation by miRNA array hybridization assay using the Affymetrix miRNA-4 gene chip as described by Barn et al., 201727. Raw data was obtained as signal intensities after the array was processed in Transcriptome Analysis Console (TAC) (Affymetrix, Sunnyvale, Calif.). Linear fold-changes in miRNA up- or down-regulation were calculated to compare the differences of all the miRNAs expressed between PTSD patients and controls. A linear fold-change of at least +/−1.5 was used as a cut off value for the inclusion of a miRNA for further analysis.

Cell Culture

THP1 cells obtained from ATCC were cultured in complete RPMI medium containing 10% FBS, penicillin, and streptomycin, HEPES buffer and 2-mercaptoethanol. The incubation condition was at 37° C. and 5% $CO_2$.

In Vitro Knockdown with siRNA in THP1 Cells

To analyze whether the presence of H3K4me3 influenced the expression of WNT 10B, KDM5B (Lysine (K)-specific demethylase 5B) was knocked down and the WNT10B transcripts quantified. THP1 cells were seeded at 2×10⁵ cells per well in a 24-well plate. After 24 hours, 5 pmol of siRNA was added as a mixture in Lipofectamine RNAiMAX (Invitrogen, ThermoFisher Scientific, USA) to each well by following the instruction from the manufacturer. The cells were further cultured for 48 hours and harvested for RNA isolation, which was later used for qRT-PCR analysis.

Micro-RNA Mimic Assay

To investigate whether hsa-miR-7113-5p regulated expression of WNT10B, miRNA mimic transfection studies were performed in THP1 cells. Mimics and inhibitors of the miRNA were obtained from Qiagen Inc. and transfected into the cells by employing Lipofectamine RNAiMAX (Invitrogen, ThermoFisher Scientific, USA). One day prior to transfection, 2×10⁵ THP1 cells were plated in a 24-well plate in 500µl complete RPMI medium. Mimic, inhibitor, and scrambled oligos were then added at an amount of 5 pmol per well. Cells were cultured for the indicated time after transfection and harvested for RNA and protein isolation. RNA samples were used for qRT-PCR based quantification of mRNAs and miRNAs. Whole-cell lysates were used for western blot analysis of miRNA target protein.

WNT10B Signaling Pathway Initiation

To analyze whether WNT 10B could influence the expression of proinflammatory genes, WNT signaling was initiated by adding recombinant human (rh)-WNT10B in PBMCs cultures. The PBMCs were isolated from healthy human individuals. Two million cells were cultured in 200 µl medium in a 96-well tissue culture plates as follows: First, the PBMCs were stimulated with Phorbol 12-myristate 13-acetate (PMA) (200 nM) for 6 hours following which, 200 ng/ml rh-WNT10B was added. Then, the PBMCs were harvested after 24 and 48 hours and used for RNA and whole cell lysate (WCL) extraction for further analysis. The culture supernatants were also collected for ELISA to detect IFNγ. The following combinations were used as controls: 1) PBMCs+PMA without WNT10B and 2) PBMCs+WNT10B without PMA.

Before activation of cells and to see whether pre-exposure of cells to WNT10B can influence inflammatory gene expression, WNT10B (200 ng/ml) was first added in all the culture with PBMCs. After 24 hours, PMA (200 nM) was added to activate the cells. The following condition was used for the control: PBMCs+WNT10B without PMA. The cells were then harvested 24 hours after addition of PMA.

To test if chronic presence of WNT 10B alone (without stimulation with PMA) can lead to increased expression of inflammatory genes in the PBMCs, PBMCs (2×10⁶ cells/well, in 200 µl, in a 96-well plate) were cultured with rh-WNT10B (200 ng/ml) for 96 hours. Additional rh-WNT10B was added after every 24 hours of culture. Cells were harvested every 24 hours for RNA and whole-cell lysate isolation. Supernatants were also collected for performing ELISA.

Blocking WNT Signaling

To investigate whether WNT10B was directly responsible for the upregulation of IFNγ expression, the WNT signaling pathway was blocked using an inhibitor of WNT response-1 (IWR-1, Sigma-Aldrich, St. Louis, Mo., cat #I0161). IWR-1 inhibits WNT signaling by stabilizing AXIN1 and prevents its degradation. AXIN1 is an inhibitor of WNT signaling pathway30. PBMCs (2×10⁶) from healthy controls were cultured overnight (~18 hours) with 10 LM of IWR-1 in separate wells of a 96-well culture plate in 200 µl complete RPMI medium. The following day, PMA and IWR-1 (in a 10 µl volume) were added to the culture to reach a final concentration of 200 nM PMA and 10 µM IWR-1, respectively. After 6 hours, WNT10B was added to the designated wells. Cells were harvested after 24 and 48 hours of adding WNT10B for total RNA extraction. Culture supernatant was collected for ELISA.

ELISA and Western Blot

ELISA for human IFNγ was performed on culture supernatants. The kit for ELISA was purchased from BioLegend Inc. (CA, USA) and assay was performed following the manufacturer's instructions. Reading for OD was performed in a Victor2TM, 1420 Multilabel Counter (Perkin Elmer, USA) plate reader.

For the Western blot, anti-human-WNT10B was purchased from SIGMA-ALDRICH (cat #PRS4619). Whole-cell lysate from THP1 cells (from 4 wells of a 24-well plate) after transfection of mimic for hsa-miR7113-5p or scramble was collected after 72 hours in a 300 μl volume of M-PER solution (ThermoFisher Scientific Inc., USA) and processed as per protocol provided by manufacturer. The total protein was not pre-quantified for loading onto the SDS-PAGE as the protein amount was to be normalized using an internal control. After SDS-PAGE, transfer of protein to nitrocellulose membrane was performed in an iBlot2 instrument (ThermoFisher Scientific Inc., USA). The primary antibody was used at 3 μg/ml of blocking agent solution (5% skimmed milk powder, BioRad Inc., USA) and incubated overnight at 4° C. Secondary antibody (Cell Signaling, cat #7074S) against rabbit IgG was used at 1:2000 dilution and incubated for 1 hour at room temperature. Protein bands were detected in a LI-COR blot detection system (Li-Cor Inc, Nebraska, USA).

Statistical Analysis

Data are presented as mean±standard deviation, with each test being repeated at least three times. A student's t test was used and p<0.05 was considered to show significant difference between the two groups under consideration. The p values were calculated by including data from three or more experiments.

Results

Results provided in the drawings and described herein are meant to be exemplary and are not intended to limit the methods and compositions to modifications or alternatives as would be understood by a person of ordinary skill in the field of endeavor.

PTSD can be associated with dysregulation of immune system related genes in the PBMCs To gain insights into whether the immune system related genes are dysregulated in PTSD patients, RNA-seq screening analysis was performed using total RNA obtained from PBMCs from healthy controls and PTSD patients, using a smaller sample size (n=5 in each group) (FIGS. 1A-1B), followed by a larger sample size to validate the genes of interest. Only genes with significant (p<0.05; student's t test), FPKM (Fragments Per Kilobase of transcript per Million mapped reads) value of at least 1 in one group and a log fold change of at least 0.5 were included in the final list for further analysis (FIGS. 1C-1D). At least 326 genes were identified that matched the criteria.

Wnt-signaling pathway genes are differentially expressed in PTSD

Figure 1G:
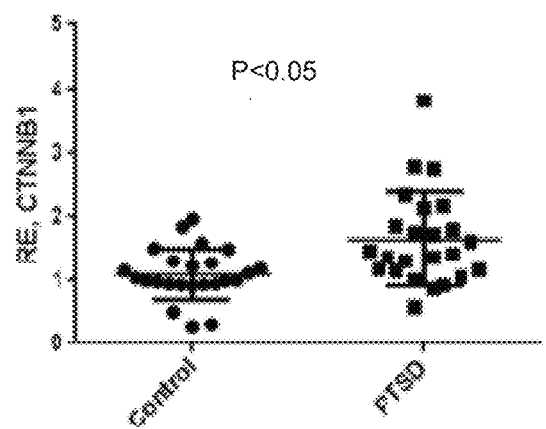
FIG. 1G illustrates a plot displaying RE of CTNNB1 for control and PTSD samples.

The expression of genes involved in cellular functions including proliferation, differentiation, polarization, and activation were examined in this example study. As shown in the Figures, the genes of the wnt-signaling pathway were significantly upregulated in the PBMCs of PTSD patients. Specifically, upregulation of certain WNT ligands including WNT10B, WNT10A and WNT7A is shown in FIG. 1C. Moreover, there were higher transcript levels of DVL1 and CTNNB1 (FIG. 1D), all of which are genes having roles downstream of the binding of WNT ligands to FZD and LRP5/6 receptors. To further support the observation on Wnt-signaling upregulation, expression of genes that inhibit this pathway was also conducted. In this regard, down regulation of TLE3 (Transducin like enhancer of split 3) is demonstrated in PTSD patients, as shown in FIG. 1E. TLE3 is among the genes that play a role in inhibiting the wnt-signaling pathway by acting as a transcriptional repressor of 0-catenin/TCF4 complex. To support the RNA-seq data, qRT-PCR validation of WNT 10B and CTNNB 1 was performed using a larger sample size consisting of 24 each of control and PTSD samples. As shown in FIGS. 1F and 1G, these genes were significantly upregulated in PTSD when compared to controls.

Higher H3K4me3 signals present in PTSD near the promoters of wnt-signaling pathway genes In order to understand the regulation of genes of the wnt-signaling pathway through epigenetic mechanisms, the H3K4me3 methylation pattern in PTSD patients was compared that in control patients. H3K4me3 ChIP sequencing was performed in 6 each of control and PTSD PBMC samples. The sequencing data was visualized in Integrated Genome Browser (IGB) for signals around genes of interest. At the genome level, there was no significant difference in the signals between controls and PTSD patients as shown in FIGS. 2A-2B, possibly indicating that there are no genome-wide alterations in H3K4me3 methylation in PTSD when compared to controls. However, when individual genes were analyzed, there is evidence of some differences in H3K4me3 signals between controls and PTSD. In particular, higher H3K4me3 methylation around (within 3 kb) the promoter regions of WNT10B, WNT10A, WNT7A, DVL1, AXIN1, and TCF7 (FIGS. 2C-2D). These data suggested that the increased expression of these genes may be contributed by the presence of higher H3K4me3 signals in PTSD patients because the presence of H3K4me3 is associated with upregulation of the nearby genes due to chromatin accessibility made easier by the methylation of histone proteins.

Knockdown of KDM5B demethylase can increase WNT10B expression

Next, the presence of H3K4me3 around WNT10B promotor was investigated as a possible control over the expression of this gene. After knockdown of KDM5B, histone demethylase specific to H3K4me3 using siRNA (FIG. 2E) gene expression indicated that WNT 10B was upregulated (FIG. 2F), thereby demonstrating that H3K4me3 was indeed involved in increasing the expression of WNT 10B.

Dysregulated miRNAs in PTSD target genes of the wnt-signaling pathway

Microarray analysis was also performed to identify potential miRNAs that are dysregulated in PBMCs of PTSD patients (FIGS. 3A-3B). Based on fold change of miRNAs, 68 miRNAs were identified with at least +/−1.5 differences in PTSD patients when compared to controls, of which 35 were upregulated and rest downregulated. A miRNA-gene interaction network analysis was performed using Ingenuity Pathway Analysis, with both sets of miRNAs obtained. The genes of wnt-signaling pathway were strongly predicted to be the targets of downregulated miRNAs indicating that upregulation of these genes in PTSD could also result from downregulation of these miRNAs (FIGS. 3C-3D). The downregulated miRNAs were investigated, and hsa-miR-7113-5p (among others) was strongly predicted to target WNT10B (FIG. 3E). This miRNA was downregulated in PTSD as per microarray analysis. To validate the microarray results, qRT-PCR was performed for hsa-miR-7113-5p in 24 samples from control and PTSD groups each and observed that it was significantly downregulated in PTSD patients when compared to controls (FIG. 3F). To show that the downregulation of hsa-miR-7113-5p can indeed lead to increased expression of WNT10B, the amount of the miRNA in THP1 cells was increased by introducing mimics of hsa-miR-7113-5p and assayed for the products of WNT10B. Significant reduction in the level of WNT10B mRNA was identified (FIG. 3G), as well as protein (FIG. 3H), after treatment of cells with miRNA mimic for the indicated time compared to scrambled miRNA and miRNA- 7113-5p-inhibitor treated groups. Together, the data show that in PTSD, there is decreased expression of miRNAs, such as hsa-miR-7113-5p, that target WNT pathway, leading to its induction.

Increase in WNT10B can increase proinflammatory cytokine gene expression

The upregulation of WNT10B was also investigated to determine if it could influence the expression level of inflammatory genes. Phorbol 12-myristate 13-acetate (PMA) stimulated PBMCs from normal controls were exposed to purified rh-WNT10B to mimic increased expression of WNT10B. Addition of rh-WNT10B to PMA activated cells led to significant increase in the expression of pro-inflammatory genes, such as Tbx-21 and IFNγ, at mRNA level at 24 hours and 48 hours (FIGS. 4A-D) and for protein level of IFNγ at 24 hours (FIG. 4E) when compared to un-activated PBMCs or PMA activated PBMCs without rh-WNT10B. It should be noted that addition of rh-WNT10B (200 and 500 ng/ml) alone to naïve PBMCs did not induce any inflammatory genes, including STAT3, STAT4, or IFNγ. These data suggested that the presence of rh-WNT10B during PBMC activation leads to enhanced induction of inflammatory cytokines.

Inhibition of WNT signaling leads to lowered expression of inflammatory cytokine Next, WNT10B signaling was tested to determine if it was involved in the upregulation of pro-inflammatory cytokine. The wnt-signaling pathway was blocked by adding IWR-1 to the culture. Upon blocking, the expression of IFNγ was significantly downregulated compared to cells activated with PMA only. Further, even the addition of WNT10B did not lead to increased expression of IFNγ and other proinflammatory genes (FIGS. 4F-4G), even after activation of PBMCs with PMA.

An example embodiment of the disclosure can include a method for treating an inflammatory disease (e.g., PTSD and/or other described herein) in a patient by delivering a wnt-signaling pathway inhibitor to the patient or to a plurality of cells extracted from the patient. Several inhibitors can include the class of IWR compounds. Generally, these compounds have a chemical structure corresponding to Structure I, which is shown below:

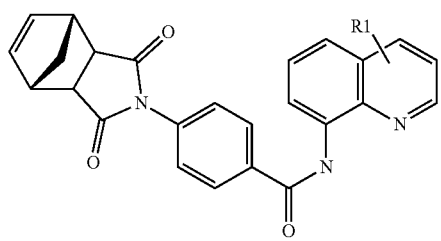

Structure I where R1 can be selected from a hydrogen, a C1-C3 alkyl group (e.g., a methyl, ethyl, or propyl group that can be linear or branched), and a halogen. Additionally, R1 can be present on any position of the quinoline ring.

In an example embodiment, the wnt-signaling pathway inhibitor can include IWR1 having R1=hydrogen at the 4 position of the quinoline ring. IWR1 has the chemical structure illustrated below:

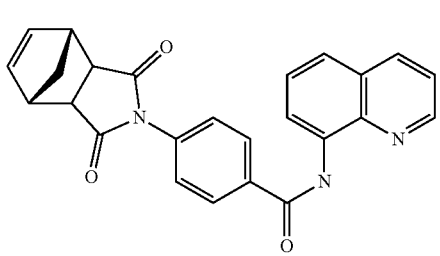

Structure II

In another example embodiment, the wnt-signaling pathway inhibitor can include IWR2 having R1=methyl group (CH$_3$) at the 4 position of the quinoline ring. IWR2 has the chemical structure illustrated below:

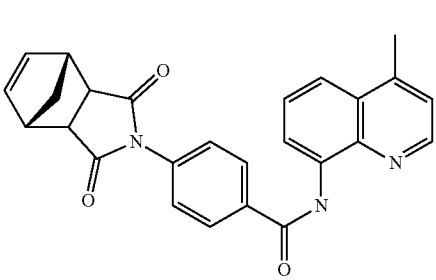

Structure III

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only and is not intended to limit the invention further described in the appended claims.

The invention claimed is:

1. A method for downregulating expression of a gene in the wnt-signaling pathway comprising:
 culturing a plurality of activated peripheral blood mononuclear cells (PBMCs);
 determining a first expression level of the gene in the wnt-signaling pathway or a protein encoded by the gene, the gene in the wnt-signaling pathway comprising WNT10B;
 contacting the culture with a micro-RNA or a micro-RNA mimic, the micro-RNA or micro-RNA mimic comprising miR-7113-5p or a micro-RNA mimic of miR-7113-5p;
 following the contact, determining a second expression level of the gene in the wnt-signaling pathway or the protein encoded by the gene; wherein
 the second expression level is lower than the first expression level.

2. The method of claim 1, further comprising isolating the plurality of PBMCs from a subject.

3. The method of claim 2, wherein the subject has been diagnosed with a condition selected from at least one of the group consisting of: PTSD, obesity, cancer, bacterial infection, rheumatoid arthritis, chronic ulcerative colitis, periodontitis, asthma, and chronic obstructive pulmonary disease.

4. The method of claim 1, wherein the plurality of PBMCs have been obtained from a subject that has been diagnosed with PTSD.

5. The method of claim 1, wherein the downregulating of the gene in the wnt-signaling pathway modifies expression of a protein encoded by the gene.

6. The method of claim 5, wherein the protein comprises Wnt-10b.

7. The method of claim 5 further comprising contacting the culture with a chemical compound.

8. The method of claim 7, wherein the chemical compound comprises 4-(1,3,3a,4,7,7a-Hexahydro-1,3-dioxo-4,7-methano-2H-isoindol-2-yl)-N-8-quinolinyl-Benzamide.

9. The method of claim 1, further comprising activating a plurality of naïve PBMCs to provide the plurality of activated PBMCs.

* * * * *